United States Patent
Talbert et al.

(10) Patent No.: US 10,499,804 B2
(45) Date of Patent: Dec. 10, 2019

(54) IMAGING SENSOR PROVIDING IMPROVED VISUALIZATION FOR SURGICAL SCOPES

(75) Inventors: Joshua D. Talbert, Cottonwood Heights, UT (US); Jeremiah D. Henley, Cottonwood Heights, UT (US); Donald M. Wichern, South Ogden, UT (US)

(73) Assignee: DePuy Synthes Products, Inc., Raynham, MA (US)

( * ) Notice: Subject to any disclaimer, the term of this patent is extended or adjusted under 35 U.S.C. 154(b) by 588 days.

(21) Appl. No.: 13/405,151

(22) Filed: Feb. 24, 2012

(65) Prior Publication Data

US 2013/0060086 A1 Mar. 7, 2013

Related U.S. Application Data

(60) Provisional application No. 61/446,481, filed on Feb. 24, 2011.

(51) Int. Cl.
*A61B 1/00* (2006.01)
*A61B 1/313* (2006.01)
*A61B 1/015* (2006.01)
*A61B 1/05* (2006.01)

(52) U.S. Cl.
CPC ........ *A61B 1/3132* (2013.01); *A61B 1/00006* (2013.01); *A61B 1/00009* (2013.01); *A61B 1/015* (2013.01); *A61B 1/05* (2013.01)

(58) Field of Classification Search
CPC ... A61B 1/126; A61B 1/0002; A61B 1/00062; A61B 1/00059; A61B 2090/0803; A61B 2560/028

USPC ......................... 600/103, 118, 156, 157, 158
See application file for complete search history.

(56) References Cited

U.S. PATENT DOCUMENTS

| | | | | |
|---|---|---|---|---|
| 5,278,642 A | * | 1/1994 | Danna | A61B 1/00096 348/269 |
| 5,400,267 A | * | 3/1995 | Denen | A61B 17/00 128/908 |
| 5,575,757 A | * | 11/1996 | Kennedy | A61B 1/00188 348/65 |
| 6,313,868 B1 | * | 11/2001 | D'Alfonso et al. | A61B 1/0002 348/72 |
| 6,638,212 B1 | * | 10/2003 | Oshima | A61B 1/0002 348/72 |
| 2004/0249267 A1 | | 12/2004 | Gilboa | |
| 2007/0030345 A1 | | 2/2007 | Amling et al. | |
| 2007/0078328 A1 | | 4/2007 | Ozaki et al. | |
| 2008/0319266 A1 | * | 12/2008 | Poll | A61B 1/00091 600/157 |
| 2009/0076534 A1 | * | 3/2009 | Shelton, IV | A61B 17/07207 606/170 |

(Continued)

*Primary Examiner* — Alexandra L Newton
*Assistant Examiner* — Rynae Boler
(74) *Attorney, Agent, or Firm* — Terrence J. Edwards; TechLaw Ventures, PLLC

(57) ABSTRACT

A system, apparatus and methods for providing a single use imaging device having improved viewing for sterile environments is disclosed and described. A single use high definition camera used for general purpose surgical procedures including, but not limited to: arthroscopic, laparoscopic, gynecologic, and urologic procedures, may comprise an imaging device that is a sterile and designed to ensure single use. The imaging device may further include a sensor located near the tip of a laparoscope and a view optimizing assembly.

20 Claims, 22 Drawing Sheets

(56) References Cited

U.S. PATENT DOCUMENTS

| | | | |
|---|---|---|---|
| 2009/0234183 A1* | 9/2009 | Abe ........................... | 600/103 |
| 2011/0037876 A1 | 2/2011 | Talbert et al. | |
| 2011/0238977 A1 | 9/2011 | Talbert et al. | |
| 2011/0270179 A1* | 11/2011 | Ouyang ............ | A61B 1/00062 |
| | | | 604/110 |
| 2012/0130160 A1* | 5/2012 | Borrye et al. ............... | 600/103 |

* cited by examiner

IMAGING SENSOR PROVIDING IMPROVED VISUALIZATION FOR SURGICAL SCOPES

CROSS-REFERENCE TO RELATED APPLICATIONS

This application claims the benefit of U.S. Provisional Application No. 61/446,481, filed Feb. 24, 2011, which is hereby incorporated by reference herein in its entirety, including but not limited to those portions that specifically appear hereinafter, the incorporation by reference being made with the following exception: In the event that any portion of the above-referenced provisional application is inconsistent with this application, this application supercedes said above-referenced provisional application.

STATEMENT REGARDING FEDERALLY SPONSORED RESEARCH OR DEVELOPMENT

Not Applicable.

BACKGROUND

Endoscopic surgery is experiencing rapid growth in the medical field. Endoscopy is a minimally invasive surgical procedure that is used to analyze the interior of a body cavity or interior surfaces of an organ by inserting a tubular member into the body cavity through a minor or minimal incision. A conventional endoscope is generally an instrument with a light source and an image sensor or device for visualizing the interior a body cavity. A wide range of applications have been developed for the general field of endoscopes including, but not necessarily limited to: arthroscope, angioscope, bronchoscope, choledochoscope, colonoscope, cytoscope, duodenoscope, enteroscope, esophagogastro-duodenoscope (gastroscope), laparoscope, laryngoscope, nasopharyngo-neproscope, sigmoidoscope, thoracoscope, and utererscope (hereinafter referred to generally as "endoscope"). The advantages of endoscopy include smaller surgical incisions and less soft tissue damage. As a result, there is significantly less discomfort and pain for the patient as well as a decrease in recovery time.

The advantages of minimally invasive surgery performed with the help of an endoscope are well known and understood in the medical field. As a result, there have been a growing number of devices for use with endoscopes for delivering, for example, diagnostic, monitoring, treatment, operating instruments, tools, and accessories (collectively, "tools") into the observation field and working space of the physician's endoscope.

As part of forming an image of the surgical site, the endoscope includes a light source and an image sensor. Endoscopes may also incorporate more than one tubular member for observation or operation within the body, such as a working channel for passing diagnostic, monitoring, treatment, or surgical tools through the endoscope. Endoscopes include glass lenses and an adjustable ocular or eye piece, a lateral connection for a light conductor, an adaptor that allows focusing, and a camera head. This configuration is also called a video endoscope.

It is axiomatic that strict sterilization of the operating room and surgical equipment is required during any surgery. The strict hygiene and sterilization conditions required in a "surgical theater," i.e., operating or treatment room, necessitate the highest possible sterility of all medical devices and equipment. Part of that sterilization process is the need to sterilize anything that comes in contact with the patient or penetrates the sterile field, including the endoscope and its attachments and components. It will be appreciated that the sterile field may be considered a specified area, such as within a tray or on a sterile towel, that is considered free of microorganisms; or the sterile field may be considered an area immediately around a patient that has been prepared for a surgical procedure. The sterile field may include the scrubbed team members, who are properly attired, and all furniture and fixtures in the area.

In recent years there has been a trend of providing a single use endoscope and components as a packaged, sterilized product, similar to a package containing a surgical implant, such as a knee or hip implant. In terms of endoscopy, instead of using endoscopes that have been reconditioned for each new surgery through traditional sterilization procedures, it means using a single use endoscope and components that are delivered to the hospital in a sterilized package. Due to this trend, it has become increasingly difficult to ensure that each endoscope and its components are properly cared for, used and sterilized for single use and not simply re-sterilized using traditional sterilization procedures.

Traditional drawbacks or problems of video endoscopes include a lack of image quality, the need for sterilization and high manufacturing cost as well as high processing cost. To address these and potentially other problems, the disclosure utilizes unique imaging devices or sensors in addition to a unique method, system and process for providing and reclaiming single use imaging devices.

Minimally invasive surgical procedures utilizing surgical scopes are desirable because they often provide one or more of the following advantages: reduced blood loss; reduced post-operative patient discomfort; shortened recovery and hospitalization time; smaller incisions; and reduced exposure of internal organs to possible contaminants.

Generally, minimally invasive surgeries utilize scopes, such as laparoscopes, that permit remote visualization of a surgical site within a patient's body while the surgical procedure is being performed. During a laparoscopic procedure, the patient's abdominal or pelvic cavity is accessed through two or more relatively small incisions rather than through a single large incision that is typical in a conventional surgery. Surgical scopes, such as laparoscopes, usually consist in part of a rigid or relatively rigid rod or shaft having an objective lens at one end and an eyepiece and/or integrated visual display at the other. The scope may also be connected to a remote visual display device or a video camera to record surgical procedures.

In laparoscopic surgeries, the abdomen is typically inflated with a gas through the use of an insufflator, to distend the abdominal space by elevating the abdominal wall above the internal organs and thereby create a sufficient working and viewing space for the surgeon. Carbon dioxide is usually used for insufflation, though other suitable gases may also be used. Conventional insufflators are adapted to cycle on and off to maintain a preset and suitable pressure within the patient's body cavity.

The local environment within a patient's abdominal space is generally rather warm and humid, and the use of devices such as harmonic scalpels and other cutting and coagulating devices generate mist, smoke, and other debris that is released into the surgical field and often becomes suspended throughout the expanded abdominal space. Additionally, blood, bodily fluids, pieces of tissue, fat or other bodily material may come in contact with or even attach to the lens. As a result of these conditions, visualization through the scope can be significantly diminished. Typically, the only solution to fogging and debris collection on the lens is removal of the scope from the body cavity and defogging or cleaning the lens by wiping it with a cloth, warming the scope tip, or utilizing another defogging method. The need to remove the scope to defog and remove debris from the lens is inconvenient for the scope operator and the surgeon and can interrupt and undesirably prolong surgical procedures.

The features and advantages of the disclosure will be set forth in the description that follows, and in part will be apparent from the description, or may be learned by the practice of the disclosure without undue experimentation. The features and advantages of the disclosure may be realized and obtained by means of the instruments and combinations particularly pointed out herein.

SUMMARY OF THE DISCLOSURE

An embodiment may comprise a single use camera used for general purpose surgical procedures including, but not limited to: arthroscopic, laparoscopic, gynecologic, and urologic. An embodiment may comprise an imaging device that is a sterile and designed to ensure single use. An embodiment may be an imaging device that comprises a single imaging sensor, either CCD (charge coupled device) or CMOS (complementary metal oxide semiconductor), encased in a molded plastic housing. The imaging device may further comprise the means to be attached to an optical coupling device, using C-Mount and CS-Mount threads or another proprietary or unique connection method. It is within the disclosure to include integrated optical systems, such that no specific coupling means is required. The imaging device may further comprise a cable or wireless method to transmit data to and from a camera control unit. An embodiment may further comprise a thermal energy dissipation means such as a heat sink or cooling mechanism.

One aspect of the disclosure provides a view optimizing assembly having a deflector assembly with critical physical, pneumatic, and optical characteristics that make possible intra-operative defogging, surgical debris deflection, and cleaning of a laparoscope lens during minimally invasive surgery, while also maintaining visualization of the surgical site. In use, the view optimizing assembly makes possible the practice of a surgical method for maintaining clear visualization of the surgical site without removing the laparoscope 12 from the abdominal cavity for the purpose of cleaning or de-fogging its lens.

Another aspect of the disclosure provides a view optimizing assembly having a quick exchange feature. In use, the quick exchange feature makes possible a surgical method for maintaining clear visualization that includes the ability to make a quick exchange of laparoscopes having different operating characteristics (e.g., laparoscopes with different tip angles, lengths, or diameters) entirely on the sterile operating field and without interference with the preexisting surgical set-up on the sterile operating field. The view optimizing assembly integrates with the existing suite of minimally invasive instrumentation. It does not interfere with the surgical set-up, and it requires minimal change in the process or practice of a surgical operating room (OR) team.

An embodiment may comprise a view optimizing assembly that may be substantially rigid or may be deformable. An embodiment may comprise a view optimizing assembly comprising a plurality of components and may comprise an imaging sensor disposed near a distal lumen opening. An embodiment may comprise a view optimizing assembly comprising fluid ports for allowing the passage of fluids therein.

In an embodiment, information will be recorded in the memory of the imaging device each time it is used in a procedure or quality control (QC) checked at the manufacturer. This information may be used to evaluate usage time, expiration date, etc. An embodiment may comprise features to ensure that the imaging device is only used once and that the imaging device is safe for use.

In an embodiment, the imaging device may be fully covered in plastic having a sensor heat sink to ensure the camera head meets cardiac floating (CF) and body floating (BF) ISO standards. An embodiment may comprise an imaging device that may be stamped with the current time when plugged into a console in the field after a quality control check has been performed. This time may be used as a baseline for usage. If the imaging device is powered off for a predetermined period of time, which may be equivalent to a sterilization cycle, then the imaging device will not function. The imaging device may display an onscreen message telling the user that the camera has already been used and will not allow current operation. These features ensure the imaging device will not be used more than one time per sterilization cycle and further ensures that proper sterilization is performed by the manufacturer or other authorized source. This function is to protect the patient and the doctor from an invalid or unsafe use.

In an embodiment an active imaging device may be attached to a control unit. The control unit will check the last sterilization date and ensure that the imaging device is no older than a predetermined safety date. If the imaging device is older than the required date, an onscreen warning will tell the user that the imaging device has expired and is unsafe for use. These features will protect the patient and the doctor from using a non-sterile imaging device.

In an embodiment a security code or some other means of identifying, and validating for use, an imaging device by a control unit maybe provided in order to verify that the imaging device is authorized for use. A validating security code or procedure of validation may be distributed to control units from a central database over the internet, by direct transfer from portable storage device such as USB device containing memory, another computer, or other storage device.

An embodiment may comprise fiberoptic bundles for light transition from a light source to near a distal lumen opening. An embodiment may comprise control unit or may comprise a light source. An embodiment may comprise data transmission cable. An embodiment may comprise a light transmission cable. An embodiment may comprise structures for deflecting fluids over and around a distal lumen opening. An embodiment may comprise an Insufflator circuit. An embodiment may be configured in a sheath form that may be configured to cover other structures.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
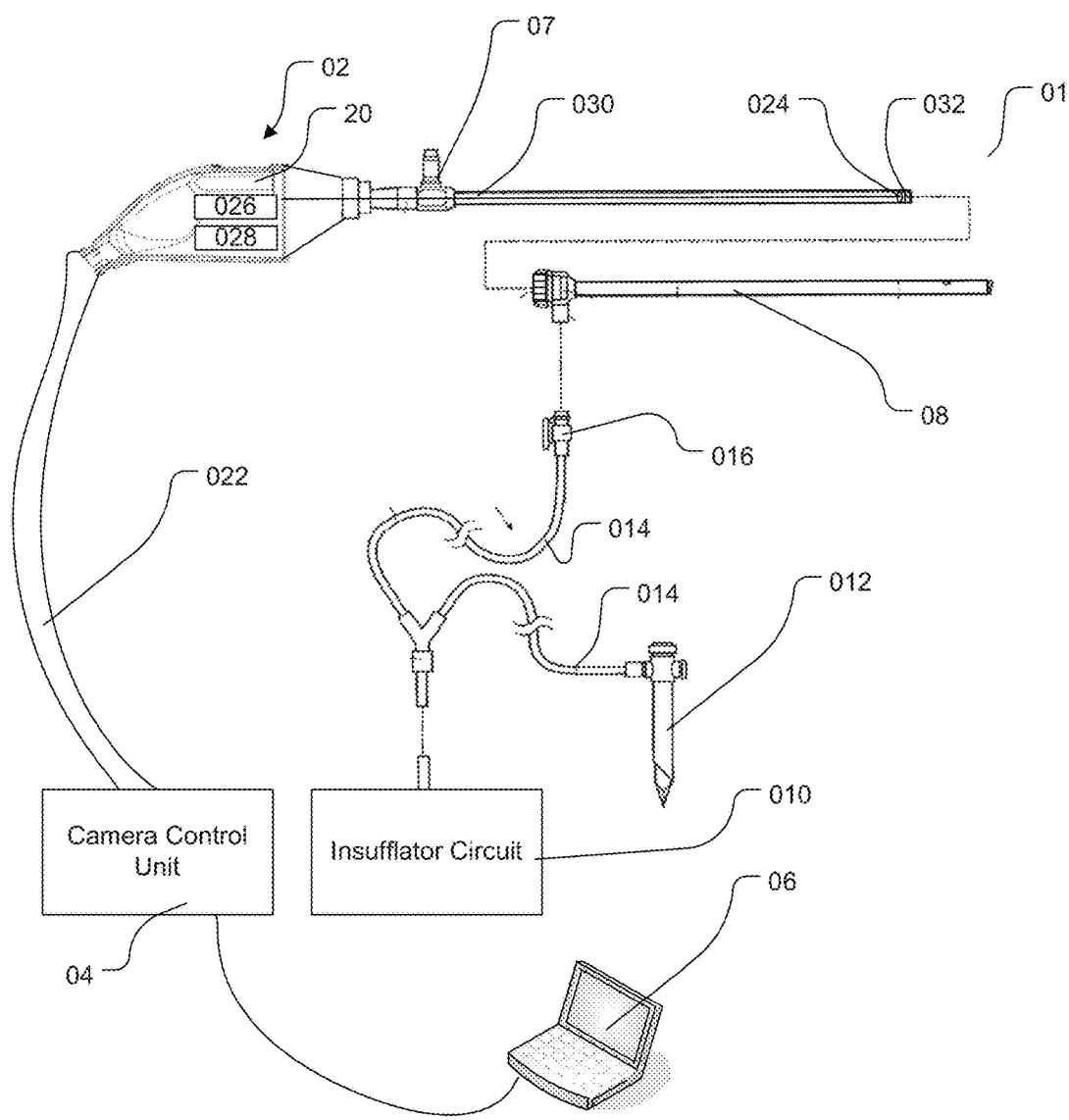
FIG. 1 is an illustration of an embodiment of an imaging system, including an imaging device and a view optimizing assembly for use with a laparoscope made in accordance with the teachings and principles of the disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

Before the devices, systems, methods and processes for providing single use imaging devices and an image or view optimizing assembly are disclosed and described, it is to be understood that this disclosure is not limited to the particular embodiments, configurations, or process steps disclosed herein as such embodiments, configurations, or process steps may vary somewhat. It is also to be understood that the terminology employed herein is used for the purpose of describing particular embodiments only and is not intended to be limiting since the scope of the disclosure will be limited only by the appended claims, if any, and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

It must be understood that "optic mount" as used herein is intended to contemplate a structure to which optics may be mounted thereto and a structure that may accept other optic mounting system, such as changeable mounting systems as commonly seen in the industry.

It must be understood that "electrically isolated" and any derivative thereof as used herein is intended to contemplate electric shielding sufficient to comply with regulations in the fields of art, and must not be construed as requiring absolute isolation.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element, step, or ingredient not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

As used herein, the term "active" as used in relation to a device or to electronic communication refers to any device or circuit, driven by hardware or software, that has decision making or logic processing capabilities regarding its operation and/or its condition. Conversely, the term "passive" as used in relation to an imaging device or to electronic communication refers to a hardware device that is written to and read from only, or a device that does not have any memory or other electronic, or physical tracking components and does not include any decision making or logic processing capabilities regarding its operation and/or its condition.

Referring now to the drawings, and specifically to FIG. 1, an embodiment of the features of the disclosure will be discussed generally. FIG. 1 illustrates a system 01 for providing a digital image using a remote imaging device 02 that may be tethered electronically and/or physically to a control unit 04. The control unit 04 may comprise a light source for the imaging device therein. The control unit 04 may be configured to exchange data with the imaging device 02 in order to provide single use functionality and safety in a sterile environment, such as an operating room, a doctor's office or dental office. Additionally, the control unit 04 may be electrically connected to a computer 06 or external monitor for increased functionality.

Figure 2:
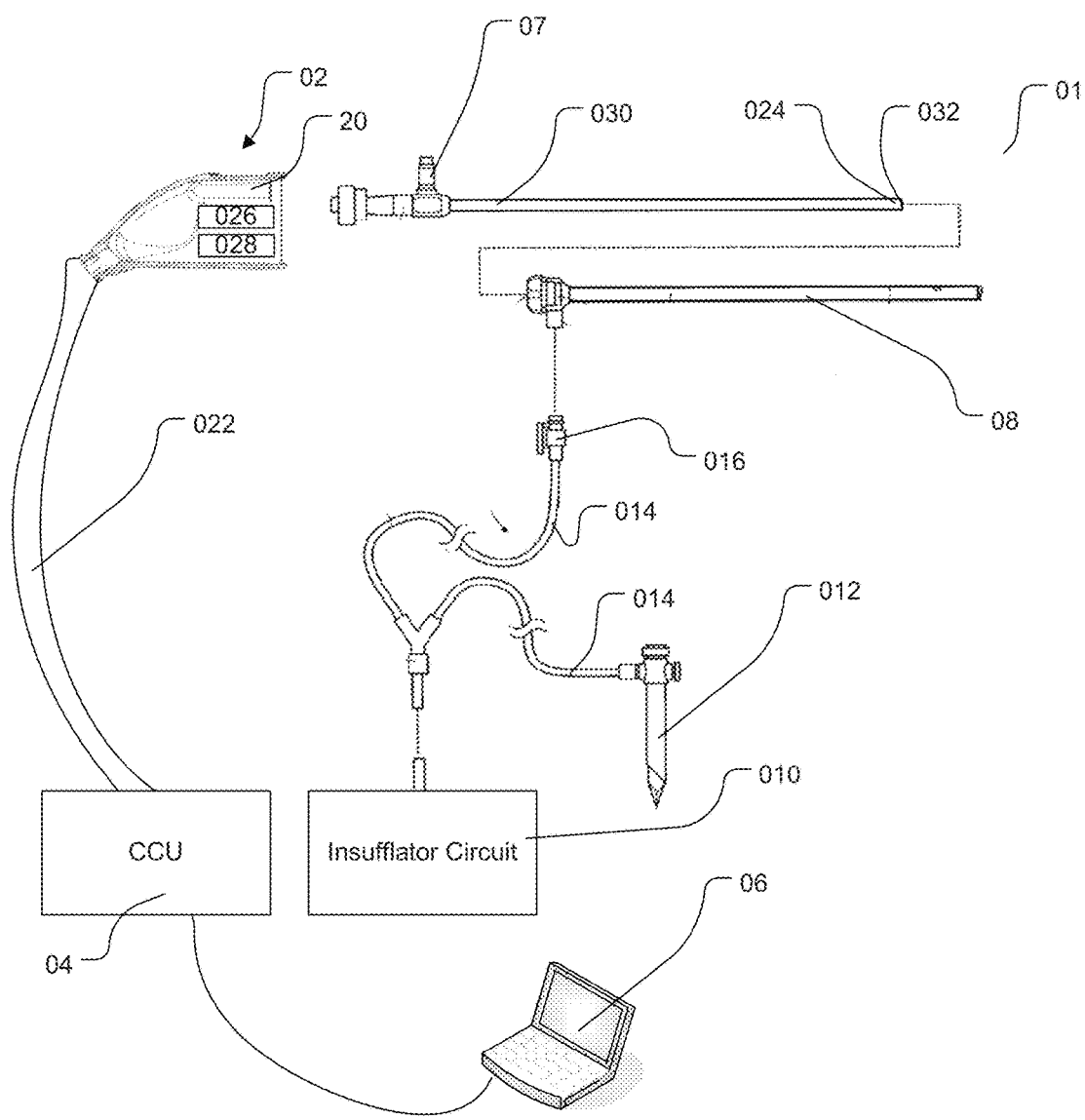
FIG. 2 is an illustration of an embodiment of an imaging system, including an imaging device and a view optimizing assembly for use with a laparoscope made in accordance with the teachings and principles of the disclosure.

The imaging device 02 may be in the form of a hand held unit with a detachable or substantially permanently attached laparoscope 07. FIG. 2 illustrates a detachable (detached) laparoscope embodiment. In order to provide increased visibility or view quality, an image optimizing assembly 08 may be used with the imaging device 02. The image optimizing assembly 08 may comprise a sheath 06021, a fluid flow channel 06026, a deflector assembly 06025, an opening in the end of the sheath 06021 for receiving a lumen 030 therethrough, and a view opening (VO) in the sheath for providing the imaging sensor access to light. The image optimizing assembly 08 may be connected to, or use fluid supplied by, an insufflator circuit 010. The insufflator circuit 010 may comprise a trocar 012 and tubing 014 with connectors 016. The ability to disconnect the imaging device 02 from the control unit 04 provides the ability to easily replace a used imaging device 02 for a sterilized, renewed imaging device 02. The imaging device 02 may have a head portion 020 generally positioned remotely from the electronic connector 022, thereby allowing greater mobility of the head portion 020 during use.

Also illustrated in FIG. 1 is an embodiment of the control unit 04 having an electronic connector therein for receiving the corresponding electronic connector 022 of the imaging device 02. The control unit 04 may also have a display for conveying information during a procedure to an operator or user. The display may also comprise interactive functionality allowing an operator to enter commands or change what information is being displayed. Such functionality may be provided by a touch screen system as is commonly known. The control unit may also have video inputs and video outputs for transferring image data to other apparatuses for increased functionality. As illustrated in FIG. 1, common apparatuses may be a computer or an external monitor.

The imaging device 02 may communicate with a control unit 04 by way of wireless transmissions such as Wifi, infrared, bluetooth etc. Other forms of wireless non-tethered connectivity may also be used for providing communication between the imaging device 02 and control unit 04, including but not limited to, radio frequency from any available spectrum, infrared of all configurations, ultrasonic, and optical. The imaging device 02 may comprise a image sensor 024 disposed within a lumen 030 of an attached laparoscopic 07, a memory 026 and associated circuitry 028, which will be discussed in greater detail below. It will be appreciated that in a surgical application, the quality of an image and the ability to adequately view the surgical site is a priority for a surgeon. The imaging sensor used may be a single sensor. Due to the ability to make smaller sized sensors, the single sensor may be located or positioned anywhere along the laparoscope or endoscope. For example, the sensor may be located or positioned proximally with respect to the endoscope, or at the distal end of the endoscope without departing from the spirit or scope of the disclosure. In an embodiment, the imaging sensor may be located on a tip of a device, i.e., in a chip-on-the-tip configuration, such as on the distal end of an endoscope or other component.

In an embodiment the image optimizing assembly 08 may use various fluids to keep vision impacting particulates from forming on to the optics 032 located near or at the tip of an endoscope lumen 030. In an embodiment an insufflator circuit may supply a fluid at pressure that is great than the ambient pressure so as to cause fluid to flow. The insufflator circuit may be the one that is used during a procedure to inflate a surgical subject during a medical procedure, and thereby be managed by an existing insufflator.

Figure 3:
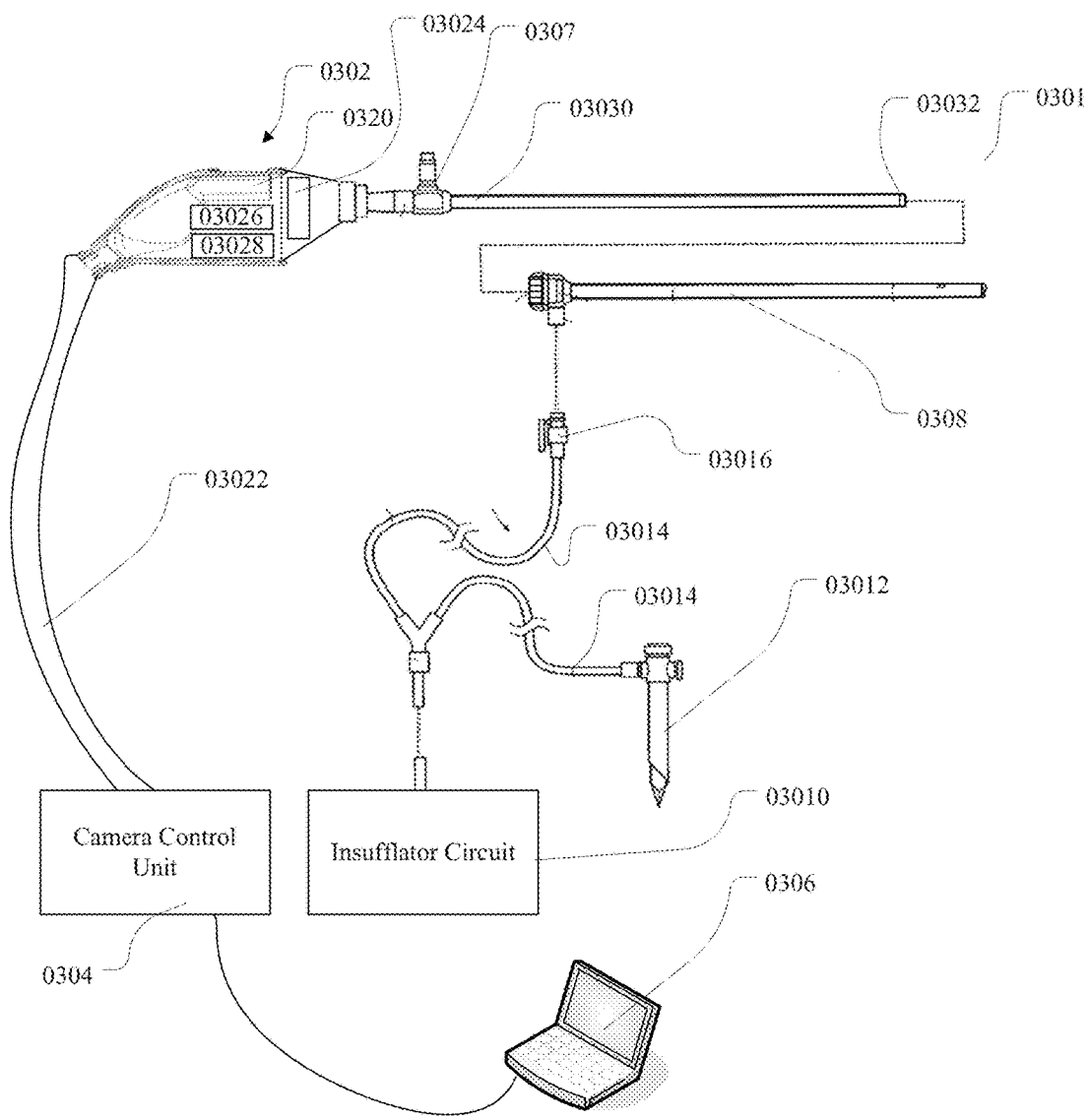
FIG. 3 is an illustration of an embodiment of an imaging system, including an imaging device and a view optimizing assembly for use with a laparoscope made in accordance with the teachings and principles of the disclosure.

Referring now to FIG. 3, an embodiment of the features of the disclosure will be discussed as they relate to an imaging device 0302 having an image sensor 03024 within the head portion 03020 of the imaging device 0302. FIG. 3 illustrates a system 0301 for providing a digital image using a remote imaging device 0302 that may be tethered electronically and/or physically to a control unit 0304. The control unit 0304 may comprise a light source for the imaging device therein. The control unit 0304 may be configured to exchange data with the imaging device 0302 in order to provide single use functionality and safety in a sterile environment, such as an operating room, a doctor's office or dental office. Additionally, the control unit 0304 may be electrically connected to a computer 0306 or external monitor for increased functionality. The imaging device 0302 may be in the form of a hand held unit with a detachable or substantially permanently attached laparoscope 0307.

In order to provide increased visibility or view quality an image optimizing assembly 0308 may be used with the imaging device 0302. The image optimizing assembly 0308 may be connected to, or use fluid supplied by, an insufflator circuit 03010. The insufflator circuit 03010 may comprise a trocar 03012 and tubing 03014 with connectors 03016. The ability to disconnect the imaging device 0302 from the control unit 0304 provides the ability to easily replace a used imaging device 0302 for a sterilized, renewed imaging device 0302. The imaging device 0302 may have a head portion 03020 generally positioned remotely from the electronic connector 03022, thereby allowing greater mobility of the head portion 03020 during use.

Also illustrated in FIG. 3 is an embodiment of the control unit 0304 having an electronic connector therein for receiving the corresponding electronic connector 03022 of the imaging device 0302. The control unit 0304 may also have a display for conveying information during a procedure to an operator or user. The display may also comprise interactive functionality allowing an operator to enter commands or change what information is being displayed. Such functionality may be provided by a touch screen system as is commonly known. The control unit may also have video inputs and video outputs for transferring image data to other apparatuses for increased functionality. As illustrated in FIG. 3, common apparatuses may be a computer or an external monitor.

The imaging device 0302 may communicate with a control unit 0304 by way of wireless transmissions such as Wifi, infrared, bluetooth etc. Other forms of wireless non-tethered connectivity may also be used for providing communication between the imaging device 0302 and control unit 0304, including but not limited to, radio frequency from any available spectrum, infrared of all configurations, ultrasonic, and optical. The imaging device 0302 may comprise a image sensor 03024 disposed within a lumen 03030 of an attached laparoscopic 0307, a memory 03026 and associated circuitry 03028, which will be discussed in greater detail below. It will be appreciated that in a surgical application, the quality of an image and the ability to adequately view the surgical site is a priority for a surgeon. The imaging sensor 03024 used may be a single sensor or made of a plurality of sensors wherein the signals of each sensor is combined to form image data. The image sensor 03024 may be disposed with the imaging device head 03020.

In an embodiment the image optimizing assembly 0308 may use various fluids to keep vision impacting particulates from forming on to the optics 03032 located near or at the tip of an endoscope lumen 03030. In an embodiment an insufflator circuit may supply a fluid at pressure that is great than the ambient pressure so as to cause fluid to flow. The insufflator circuit may be the one that is used during a procedure to inflate a surgical subject during a medical procedure, and thereby be managed by an existing insufflator.

Figure 4:
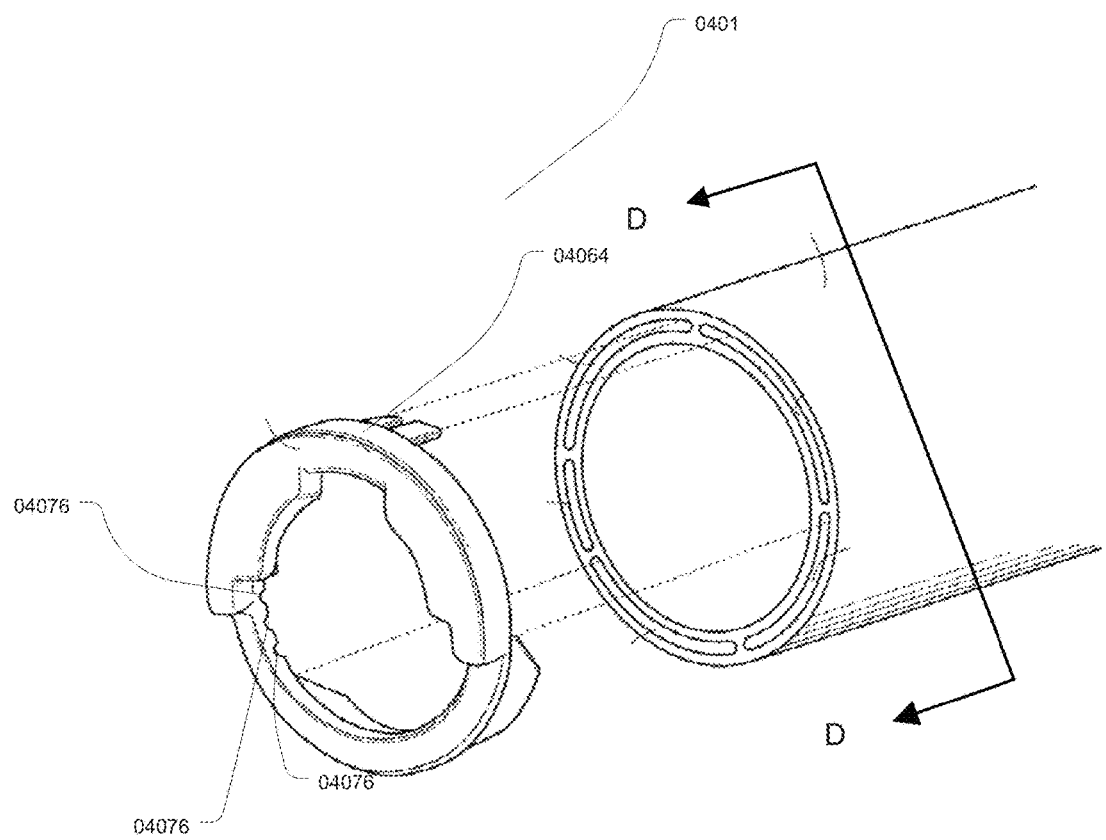
FIG. 4 is an illustration of an embodiment of a view optimizing assembly for use with a laparoscope made in accordance with the teachings and principles of the disclosure.

FIG. 4 illustrates a detailed view a deflector assembly. A deflector assembly 0401 may be disposed on a tip of a view optimizing assembly 08 of FIG. 1 in order to control the fluid flow characteristics around an optical element that is disposed on the tip of a corresponding lumen of a laparoscopic device. The deflector assembly 04064 directs a sterile fluid or air along a plurality of individual diverging channels 04076 (three are shown). The diverging channels 04076 may distribute bursts or steady flow of sterile fluid or air in a spreading pattern across the optical element (lens) disposed on the tip of a laparoscope. In the illustrative embodiment, the diverging channels 04076 discharge bursts of sterile fluid or air in a path up to 90 degrees of the original fluid flow in order to provide a relatively laminar fluid flow over the lens. A path direction change that is greater than 90 degrees may cause too much turbulence and pressure loss in the region around the lens or optical element. Fluids that are typically used are, CO2 gas, air and saline liquid. It is within the scope of this disclosure to contemplate the use of any typically available fluid, whether it is a liquid or a gas. As the fluid changes in density, its flow characteristics may change as well and will need to be directed at different angles of an optical element.

Figure 5:
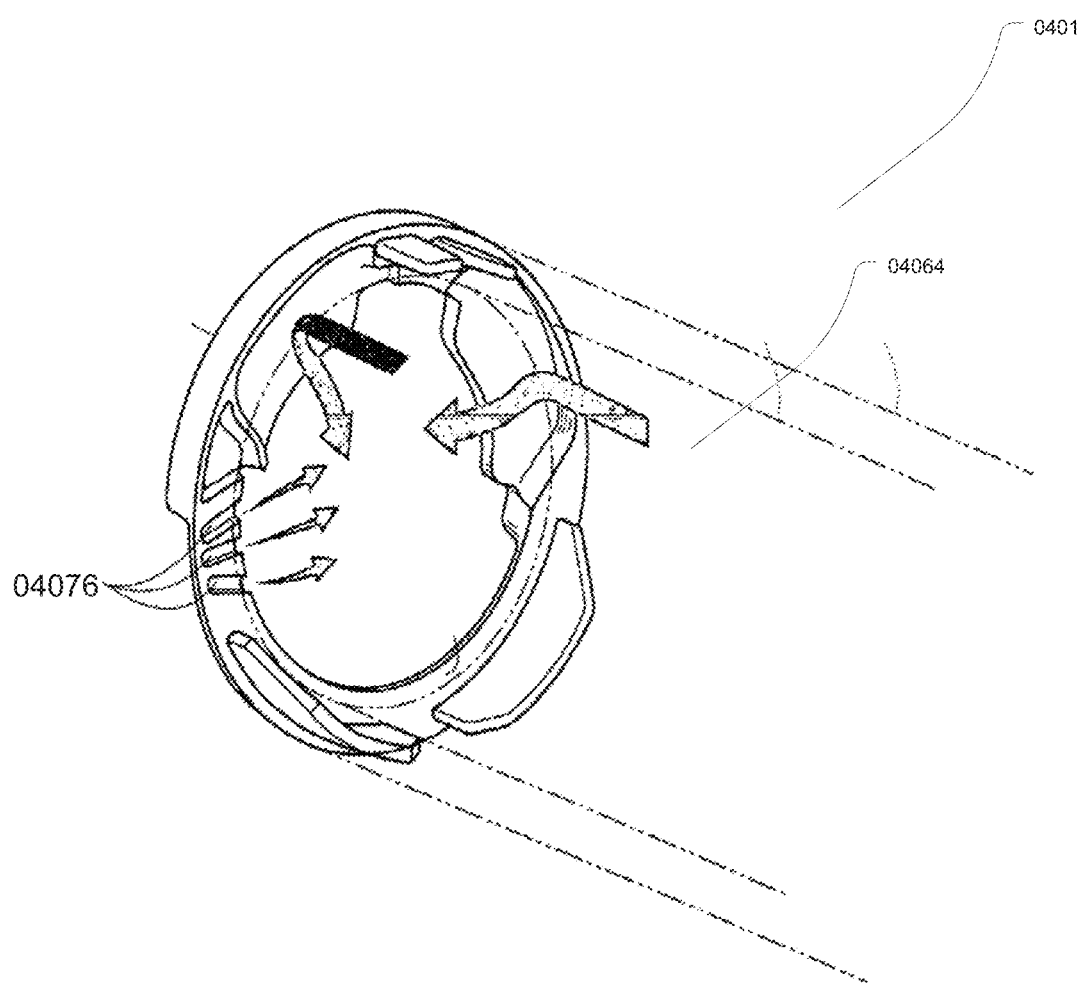
FIG. 5 is a schematic view of a view optimizing assembly for use with a laparoscope having a zero degree shaft tip.

FIG. 5 illustrates the back side of the deflector assembly of FIG. 4. As can be seen in FIG. 5, the arrows represent fluid flow and the typical way that a fluid may be directed over an optical element. The fluid may be supplied by way of an insufflator circuit that is being used in the surgery to inflate a body cavity, or it may be supplied separately. The deflector assembly may be configured for attachment at the distal end of the sheath of the view optimizing assembly so that when a laparoscopic lumen is sheathed with the view optimizing assembly the deflector assembly is disposed near to an optical element.

Figure 6:
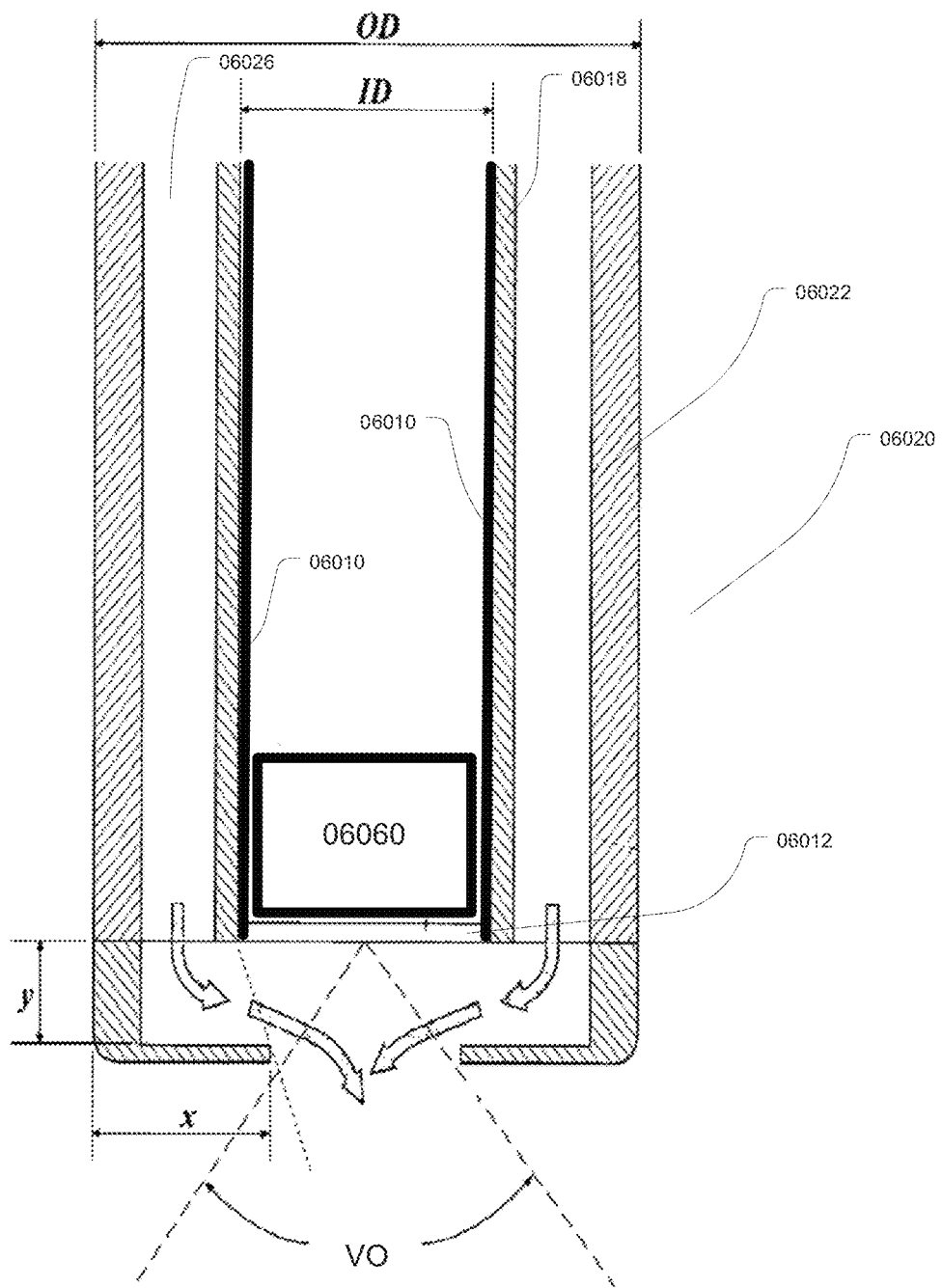
FIG. 6 is a schematic view of a deflector assembly illustrating fluid flow where arrows represent a fluid used in the system in accordance with the teachings and principles of the disclosure.

FIG. 6 illustrates a cut away view of a laparoscopic lumen sheathed with in a view optimizing assembly. It should be noted that the cut away is defined by D-D of FIG. 4. The lumen walls 06010 can be seen having an optical element 06012 disposed at the tip thereof. Additionally, an image sensor 06060 can also be seen located at, or near, the tip of the lumen walls 06010. The optical element 06012 may be configured to properly convey light to the image sensor 06060. The inner wall 06018 of the view optimizing assembly 06020 and the outer wall 06022 have a space disposed between them that forms a fluid flow channel 06026. As can be seen in the figure, a fluid (represented by the arrows shown) flows down the fluid flow channel 06026 toward an outlet at the tip. The outlet at the tip also serves as a view opening (VO) and is configured to allow light to reach or access the image sensor 06060. As is illustrated by the differing direction of the cross hatching as the outer wall 06022 approaches the tip, a deflector assembly 06025. The deflector assembly 06025 may provide fluid deflection flow channels that are illustrated by "y" and "x" as can be seen in the figure. By varying the dimensions of "y" and "x" the clearing effect if the fluid can be controlled. For example, the relationship between "x" and "y" can control the laminar and turbulent flow across the face surface of the optical element 06012. Additionally, it should be noted the inside diameter (ID) should be larger than the diameter of the laparoscopic lumen. It should also be noted that the outside diameter (OD) of the sheath 06020 should be held to industry standards.

Figure 7:
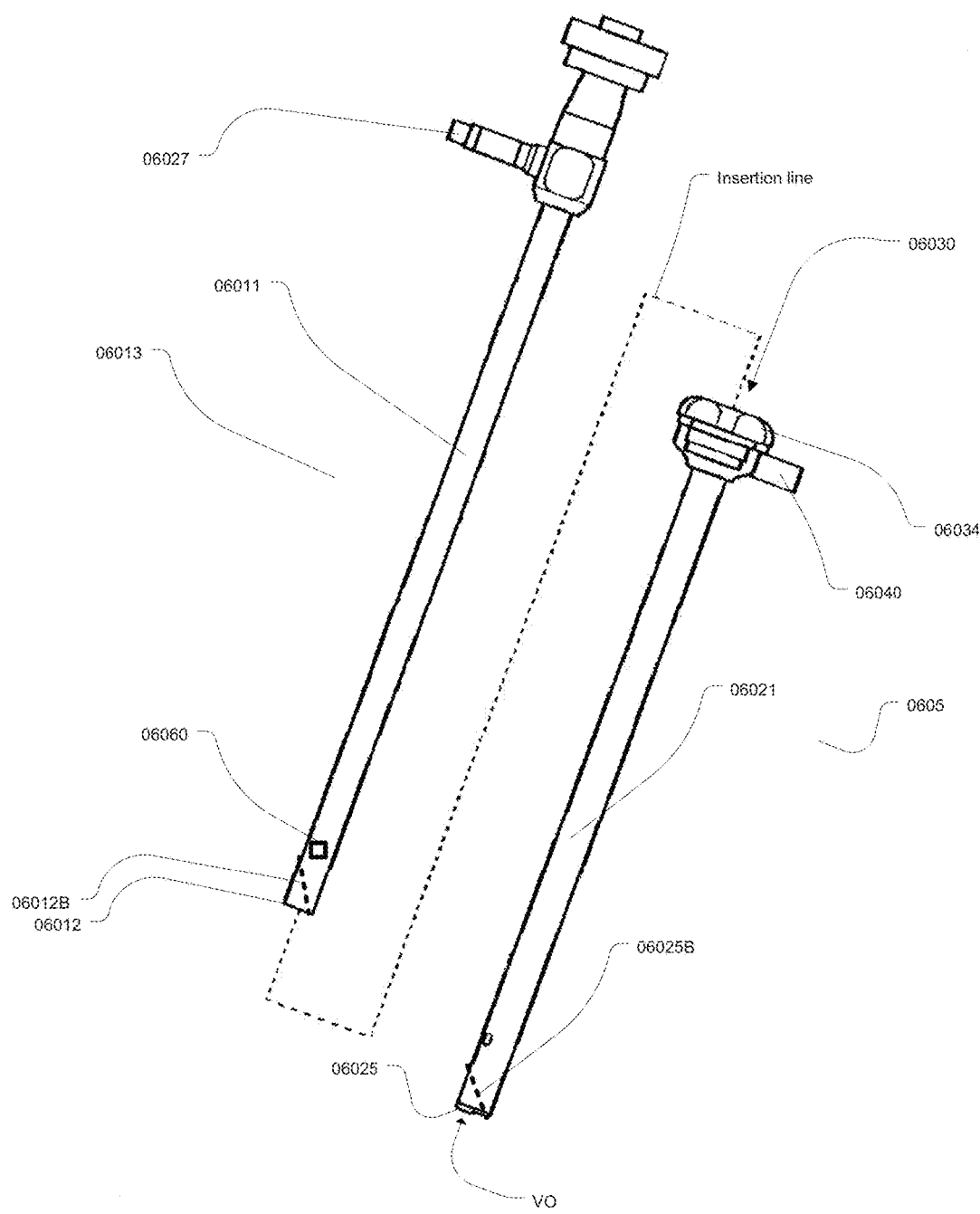
FIG. 7 is a cross-sectional view of an embodiment of a sheath of a view optimizing assembly and a laparoscope illustrating a fluid flow diagram in accordance with the teachings and principles of the disclosure.

FIG. 7 illustrates the sheathing configuration of the view optimizing assembly 0605 as it relates to a laparoscopic device 06013 having a lumen 06011 sheathed with in a view optimizing assembly. The lumen 06011 can be seen having an optical element 06012 disposed at the tip thereof. In various embodiments it may be desirable to have differing tip angles as is depicted by the angle dashed line labeled 06012B, which schematically illustrates an angled optical element. Additionally, an image sensor 06060 can also be seen located at, or near, the tip of the lumen 06011. The optical element 06012 may be configured to properly convey light to the image sensor 06060. The laparoscopic device 06013 may have light port 06027 for providing light into the device. As illustrated, a dotted insertion line shows the sheathing relationship between the laparoscopic device 06013 and the view optimizing assembly 06020. The insertion line directs the lumen 06011 into the opening 06030 disposed at one end of the view optimizing assembly 06020. Additionally, it should be noted the inside diameter of the view optimizing assembly 06020 should be larger than the diameter of the laparoscopic lumen. A lock 06034 may be provided configured to keep the view optimizing assembly 06020 in place during use. The inner wall of the view optimizing assembly 06020 and the outer wall define a sheath 06021 that is configured that may substantially cover or sheath the lumen 06011 of the laparoscopic device 06013. The walls have a space disposed between them that forms a fluid flow channel 06026 as seen in FIG. 6. A fluid inlet port 06040 may be provided to allow fluid into the device. As can be seen in FIG. 6, a fluid (represented by the arrows shown) flows down the fluid flow channel 06026 toward an outlet at the tip. The outlet at the tip also serves as a view opening (VO) and is configured to allow light to reach or access the image sensor 06060. The deflector assembly 06025 may provide fluid deflection flow channels for directing the clearing effect across the face surface of the optical element 06012. As illustrated by dashed line 06025B, the tip angle of the view optimizing assembly 0605 may be varied to correspond to the optical element 06012B of the lumen 06011.

Figure 8:
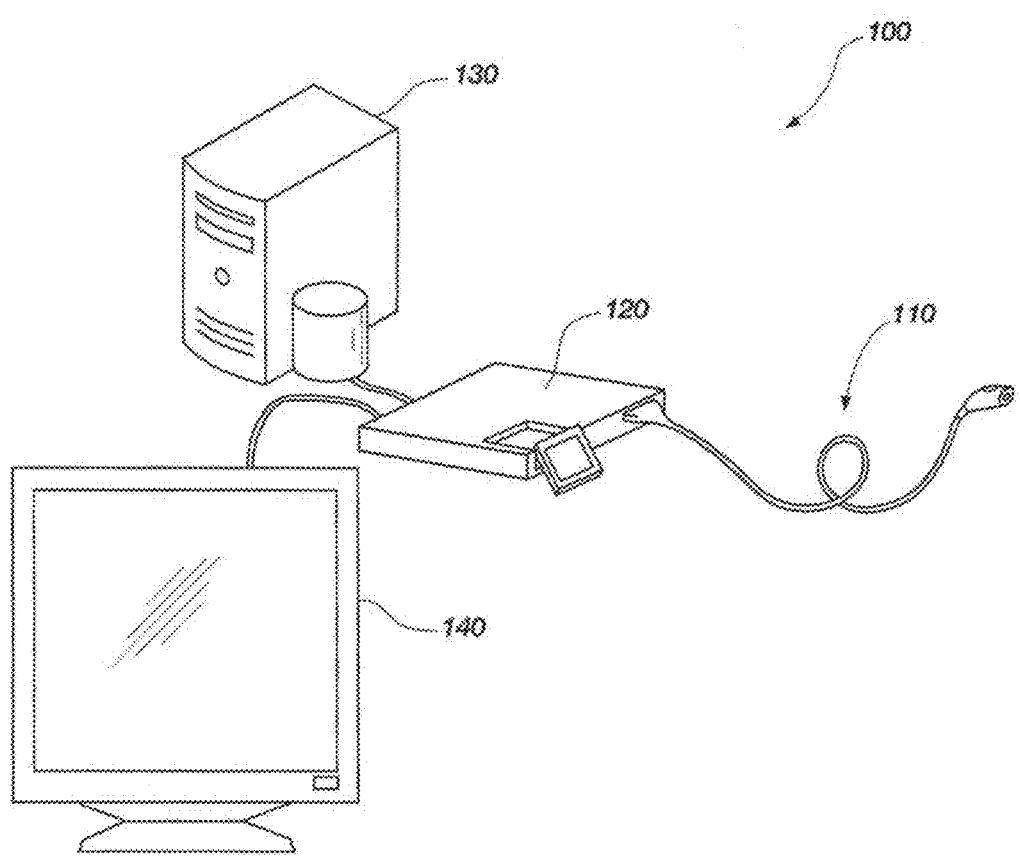
FIG. 8 is an illustration of an embodiment of the features of the disclosure and made in accordance with the teachings and principles of the disclosure.

Referring now to FIG. 8, an embodiment of the features of the disclosure will be discussed generally. FIG. 8 illustrates a system 100 for providing a digital image using a remote imaging device 110 that may be tethered electronically and physically to a control unit 120. The control unit 120 may be configured to exchange data with imaging device 110 in order to provide single use functionality and safety in a sterile environment, such as an operating room, a doctor's office or dental office. Additionally, the control unit 120 may be electrically connected to a computer 130 or external monitor 140 for increased functionality.

Figure 9:
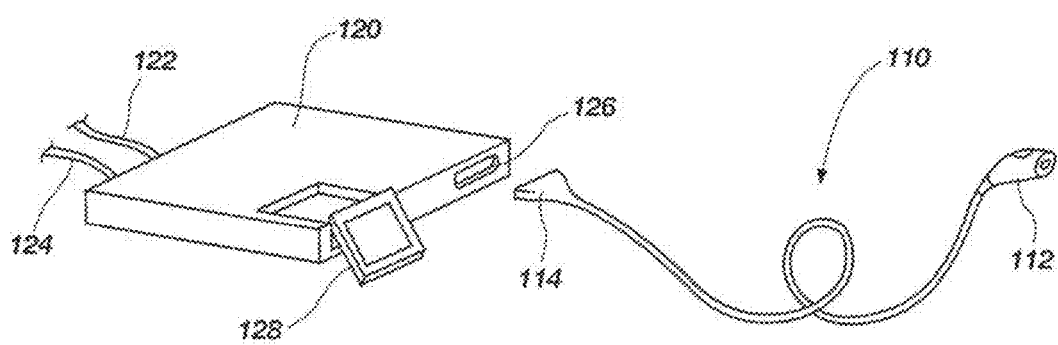
FIG. 9 is an illustration of an embodiment of an imaging system made in accordance with the teachings and principles of the disclosure.

Referring now to FIG. 9 where the imaging system 100 will be discussed in greater detail. As is illustrated in FIG. 9, the imaging device 110 can be connected or disconnected from the control unit 120 by way of an electronic connector 114 on the imaging device 110 that is configured to electronically and physically interact with a corresponding electronic connector 126 on the control unit 120. The ability to disconnect the imaging device 110 from the control unit 120 provides the ability to easily replace a used imaging device 110 for a sterilized, renewed imaging device 110. The imaging device 110 may have a head portion 112 generally positioned remotely from the electronic connector 114, thereby allowing greater mobility of the head portion 112 during use.

Also illustrated in FIG. 9 is an embodiment of the control unit 120 having an electronic connector 126 therein for receiving the corresponding electronic connector 114 of the imaging device 110. The control unit 120 may also have a display 128 for conveying information during a procedure to an operator or user. The display 128 may also comprise interactive functionality allowing an operator to enter commands or change what information is being displayed. Such functionality may be provided by a touch screen system as is commonly known. The control unit may also have video inputs 122 and video outputs 124 for transferring image data to other apparatuses for increased functionality. As illustrated in FIG. 8, common apparatuses may be a computer 130 or an external monitor 140.

Figure 10:
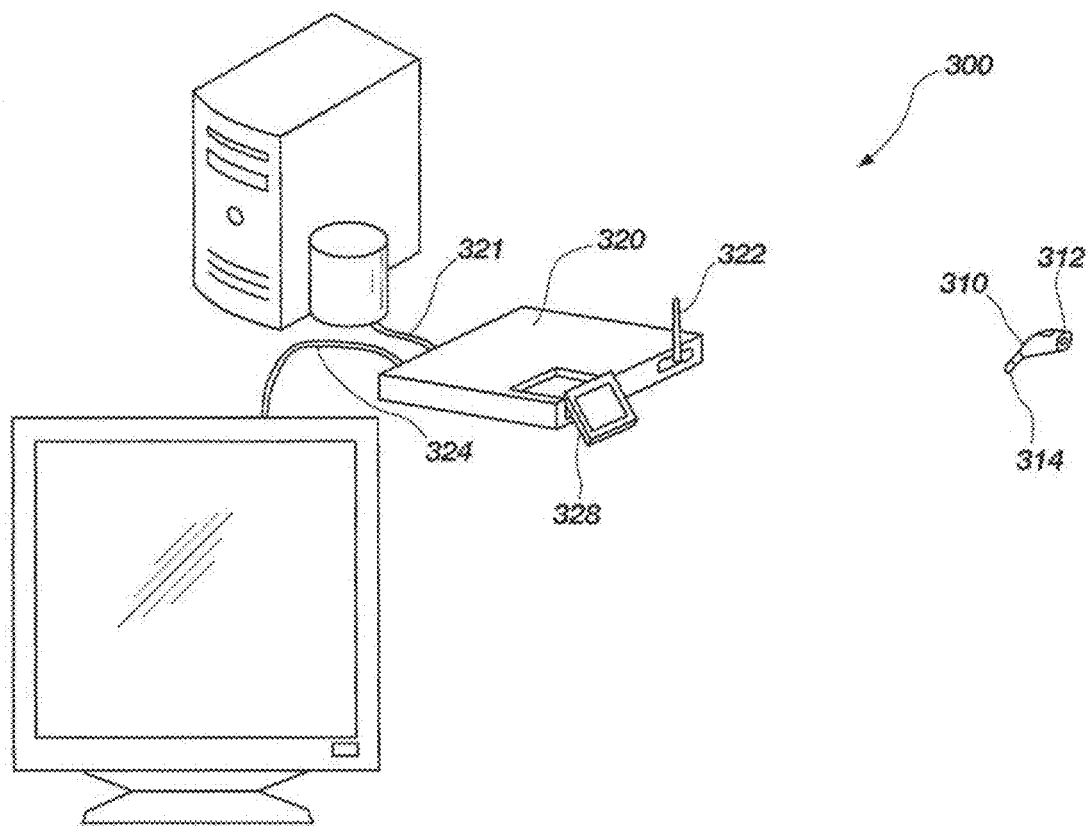
FIG. 10 is an illustration of an imaging system having wireless features made in accordance with the teachings and principles of the disclosure.

Referring now to FIG. 10 an imaging system 300 will be discussed having wireless capability and features. As is illustrated in FIG. 10, the imaging device 310 may communicate with a control unit 320 by way of wireless transmissions such as Wifi, infrared, bluetooth etc. Other forms of wireless non-tethered connectivity may also be used for providing communication between the imaging device 310 and control unit 320, including but not limited to, radio frequency from any available spectrum, infrared of all configurations, ultrasonic, and optical. The imaging device 310 may comprise a head portion 312 that houses an imaging sensor, memory and associated circuitry, which will be discussed in greater detail below. The head portion 312 may further comprise a wireless transceiver 314 for communicating with a corresponding wireless transceiver 322 housed in the control unit 320. The ability to separate the head portion 312 from the control unit 320 via wireless transmissions may provide for the easy replacement of used imaging devices for sterilized and renewed imaging devices. In other words, the wireless communication may be enabled by an electronic communication circuit that is a wireless communication transceiver configured to communicate wirelessly with a corresponding transceiver on said control unit using any of the above noted wireless technologies. The wireless functionality also allows for greater mobility of the head portion 312 during use. It will be appreciated that the wireless features and functionality may be incorporated into any of the embodiments disclosed herein or embodiments that fall within the scope of this disclosure.

Also illustrated in FIG. 10 is an embodiment of the control unit 320 having wireless capabilities and features. A transceiver 322 may be provided in or as part of the control unit 320 for receiving and transmitting wireless data to the imaging device 310. The control unit 320 may also have a display 328 for conveying information during a procedure to an operator or user. The display 328 may also comprise interactive functionality allowing an operator to enter commands or change what information is being displayed. Such functionality may be provided by a touch screen system as is commonly known. The control unit 320 may also have video inputs 321 and video outputs 324 for transferring image data to other apparatuses for increased functionality. As illustrated in FIG. 8 common apparatuses may be a computer 130 or an external monitor 140. It is within the scope of this disclosure to include an imaging system comprising both wired and wireless communication capabilities.

Figure 11:
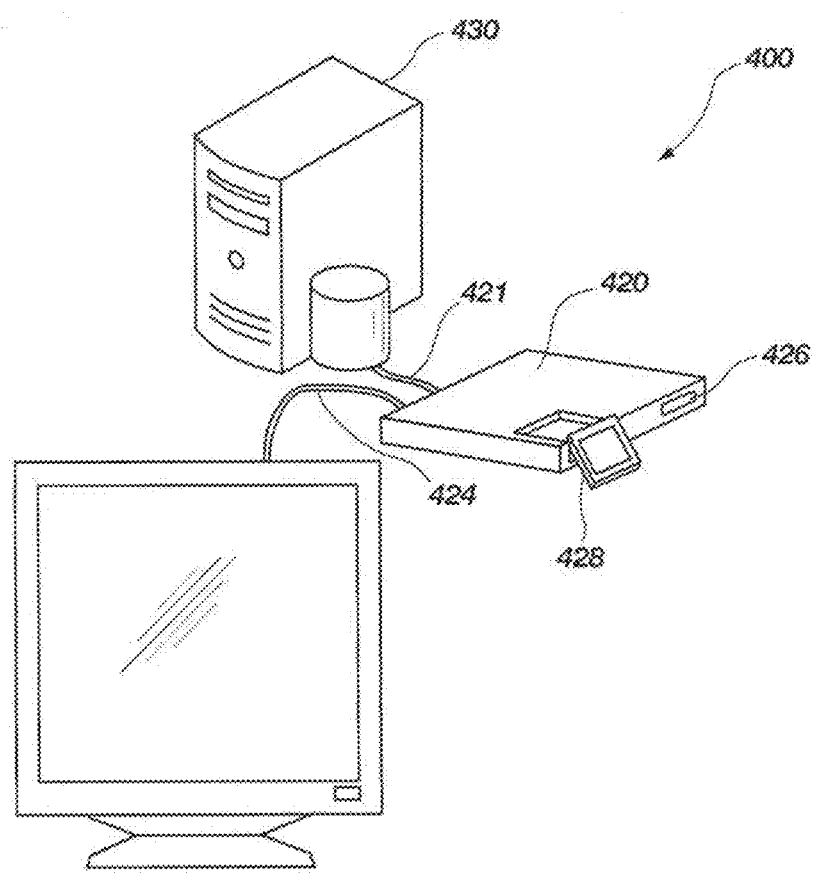
FIG. 11 is an illustration of an embodiment of a control unit disconnected from an imaging device, but illustrated as remaining connected to complementary apparatuses, and made in accordance with the teachings and principles of the disclosure.

Illustrated in FIG. 11 is an embodiment of the control unit 420 disconnected from an imaging device that is illustrated as being connected to complementary apparatuses. A connector 426 may be provided therein for transferring data to and from an imaging device. The ability to separate the imaging device may provide for the easy replacement of used imaging devices with sterilized and renewed imaging devices. The control unit 420 may also have a display 428 for conveying to an operator information during a procedure. The display 428 may also comprise interactive functionality allowing an operator to enter commands or change what information is being displayed. Such functionality may be provided by a touch screen system as is commonly known. The control unit may also have video inputs 421 and video outputs 424 for transferring image data to other apparatuses for increased functionality. Common apparatuses may be a computer 430 or an external monitor 440 there by increasing the technical functionality of the system 400. A computer 430 may be used for storing the digital output from the imaging system or may be used to enhance and provide further adjustment within the system. An external monitor 440 may be used to show real time digital images to aid an operator in the use of the system, or later review and study the recorded digital imagery.

Figure 12:
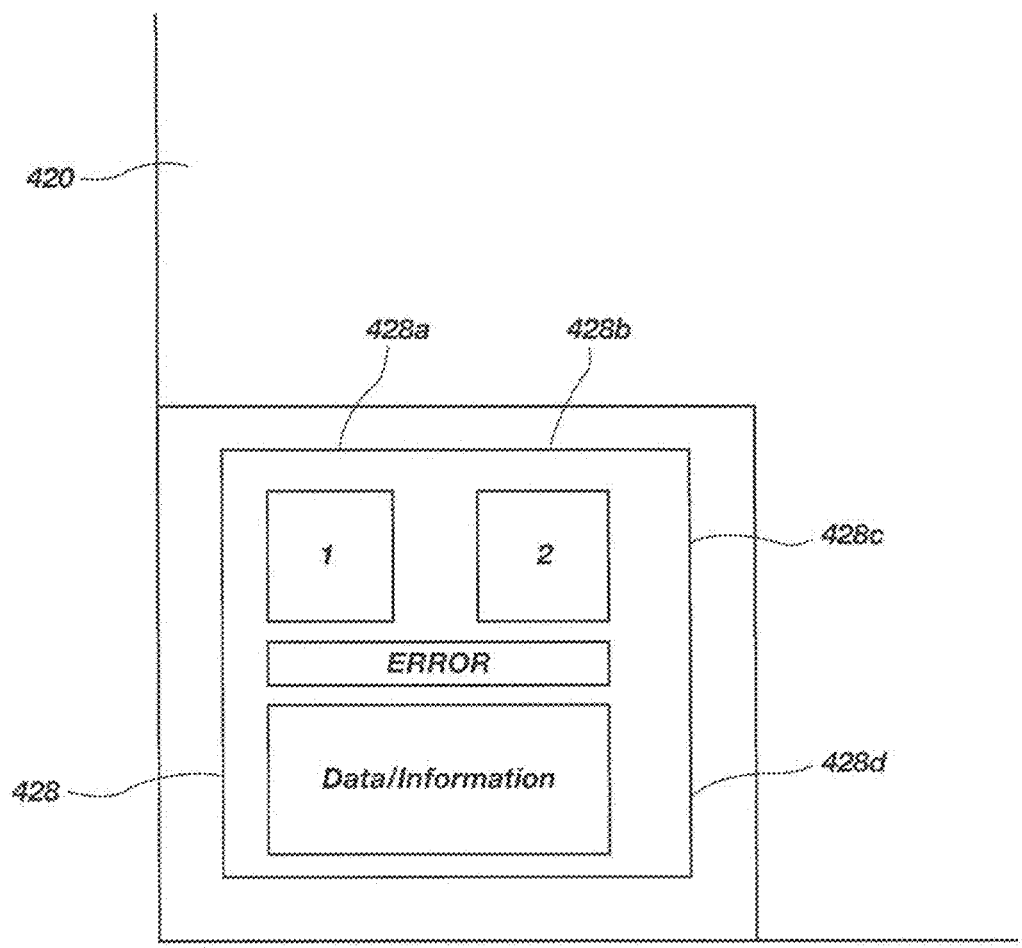
FIG. 12 is an illustration of an embodiment of a control unit display made in accordance with the teachings and principles of the disclosure.

Referring now to FIG. 12 an embodiment of a control unit display 428 that may be part of a control unit 420 will be discussed in greater detail. The display 428 may be a digital display of liquid crystal design (LCD), or the display may be some other technology beside LCD, and may have touch screen functionality and capability for an operator or user to input commands into the system 400. The embodiment discussed herein may have input portions 428a and 428b whereby an operator or user may input commands into the system 400. The embodiment may further comprise a status portion 428c informing a user about the operational status of the components of the system 400. For example, display portion 428c may display an error message related to the condition of an attached imaging device 410 if the imaging device 410 has already been used or has been deemed unfit for a procedure. The display 428 may also have a dedicated message portion 428d providing instructions and further information to an operator or user. The configuration of the display 428 may change during use to accommodate further functionality. A plurality of displays 428 is contemplated by, and falls within the scope of, this disclosure and may be used alternatively or in conjunction with this embodiment. An embodiment may comprise a key pad or a button pad for control purposes within a control unit.

Figure 13:
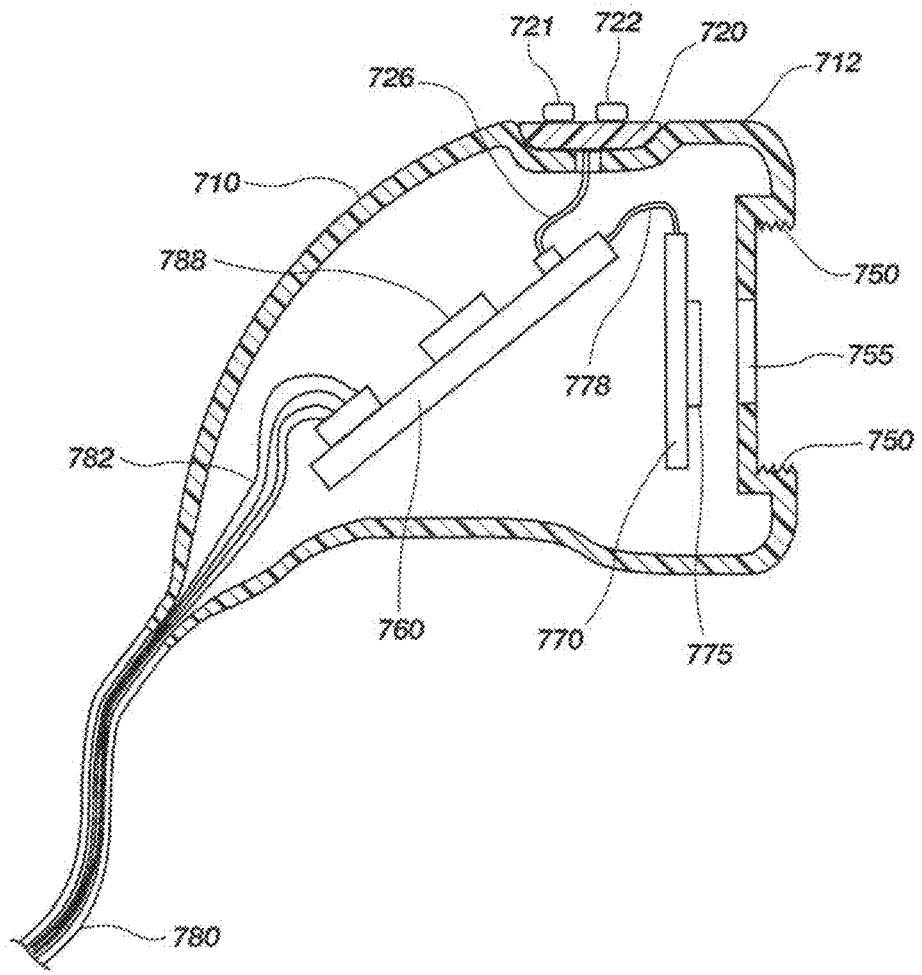
FIG. 13 is a cross-sectional view of an embodiment of an imaging device head made in accordance with the teachings and principles of the disclosure.

Illustrated in FIG. 13 is a cross-sectional view of an embodiment of an imaging device head 712. The imaging device head 712 may comprise a housing 710 made of a suitably rigid material, such as plastic or metal. The housing 710 may be sealed against fluids and gases so as to protect the internal circuitry and provide a suitable surface for sterilization and renewal. The imaging device head 712 may further comprise a user input panel 720 having buttons 721 and 722 for operation of the imaging device head 712. Additional, buttons may be provided and the functionality of the buttons can be customized for a given procedure or a given operator. The control panel 720 may be internally connected to other circuitry of the imaging device head 712 by an electrical connector 726.

As illustrated further in FIG. 13, imaging device head 712 may comprise an optical mount system 750, such as a C-mount system for receiving threaded accessories, for example one inch threaded accessories. A window 755 may also be incorporated into the embodiment for facilitating the transmission of light from an optical accessory to an image sensor 775. The image sensor 775 may be mounted to a supporting printed circuit board or supportive substrate 770. An electronic connector 778 may be incorporated to electronically connect the image sensor 775 to a main circuit or main printed circuit board 760. A main wiring harness 782 may be incorporated into a wired tether 780 thereby electrically connecting the components of the imaging device head 712 to a control unit.

The imaging device head 712 may further comprise a memory 788 or memory circuit allowing the storage of data within the imaging device head 712. It will be appreciated that memory may be any data storage device that is capable of recording (storing) information (data). Data that may be stored or written into memory 788 may include an identifying serial number that uniquely identifies an imaging device. Other data that may be stored or written into memory 788 may include data such as the amount of the time the imaging device has been used, i.e., the hours of operation, or the amount of time the imaging device has been powered on. Data that may be written into memory 788 may include sterilization data or renewal data, representing the working condition of the imaging device. Data that may be stored or written into memory 788 may include data such as manufacturing date, date of last verification or quality control check, location of manufacture, i.e., may include name, city, state, street address and so forth, last control unit that the imaging device head was attached to, imaging device head diagnostic information, specific procedural settings for the imaging device head, or preferred settings for an operator or user, such as a surgeon. Data representing the above characteristics, or other indicia, of the imaging device may be recorded into memory within the imaging device.

The memory 788 may be encryption protected so as to avoid tampering or unintended use and foreseeable misuse. It should be noted that a memory 788 may be placed anywhere in the imaging device and not just the imaging device head without departing from the scope of the disclosure. The memory 788 may comprise a permanent or semi-permanent portion allowing varying degrees of data durability.

Figure 14:
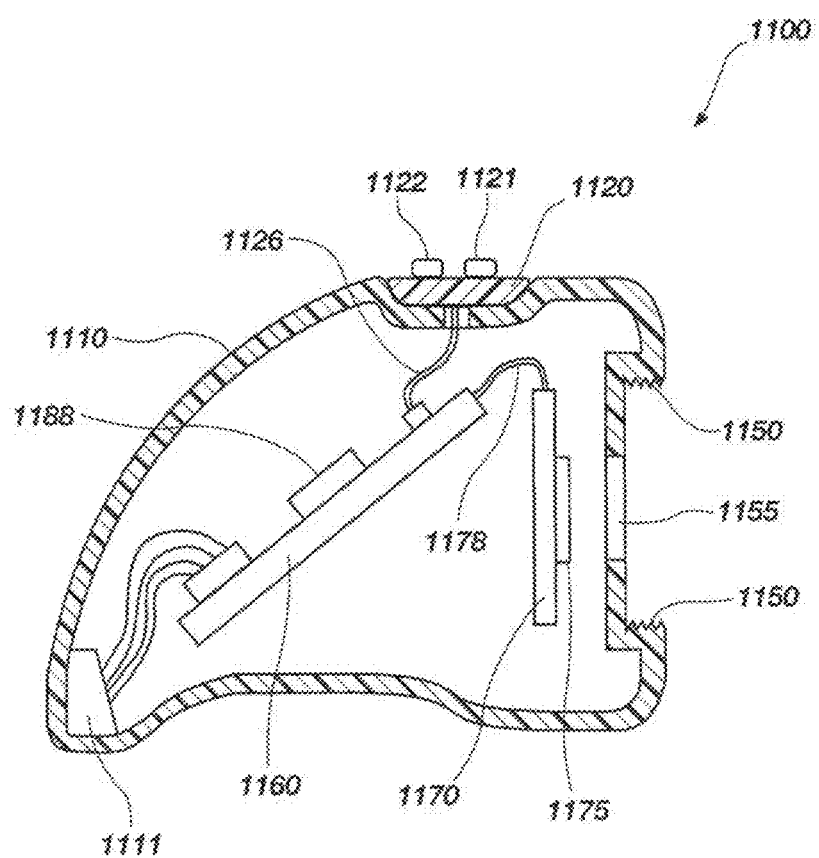
FIG. 14 is a cross-sectional view of an embodiment of an imaging device head made in accordance with the teachings and principles of the disclosure.

With reference to FIG. 14, an embodiment of an imaging device 1100 comprising wireless transmission functionality will be discussed. A cross-sectional view of an embodiment of an imaging device head 1112 is shown in FIG. 14. The imaging device head 1112 may comprise a housing 1110 made of a suitably rigid material such as plastic or metal. The housing 1110 may be sealed against fluids and gases so as to protect the internal circuitry and provide a suitable surface for sterilization and renewal. The imaging device head 1112 may further comprise a user input panel 1120 having buttons 1121 and 1122. Additional, buttons may be provided and the functionality of the buttons can be customized for a given procedure and or a given operator. The control panel 1120 may be internally connected to other circuitry of the imaging device head 1112 by an electrical connector 1126. The imaging device head 1112 may communicate with a control unit by way of wireless transmissions such as Wifi, infrared, bluetooth etc. Other forms of wireless non-tethered connectivity may also be used for providing communication between the imaging device head 1112 and the control unit, including but not limited to, radio frequency from any available spectrum, infrared of any configuration, ultrasonic, and optical.

As illustrated further in the embodiment of FIG. 14, the imaging device head 1112 may comprise an optical mount system 1150, such as a C-mount system for receiving threaded accessories, for example one inch threaded accessories. A window 1155 may also be incorporated into the embodiment for facilitating the transmission of light from an optical accessory to an image sensor 1175. The image sensor 1175 may be mounted to a supporting printed circuit board or supportive substrate 1170. An electronic connector 1178 may be incorporated to electronically connect the image sensor 1175 to a main circuit or main printed circuit board 1160. The circuitry of the imaging device head 1112 may electrically be connected to a wireless transceiver 1111 for transmitting and receiving data from a wirelessly configured control unit as illustrated in FIG. 10.

The imaging device head 1112 may further comprise a memory 1188 or memory circuit allowing the storage of data within the imaging device head 1112. Data that may be stored or written into memory 1188 may include an identifying serial number that uniquely identifies an imaging device. Other data that may be stored or written into memory 1188 may include data such as the amount of the time the imaging device has been used, i.e., the hours of operation, or the amount of time the imaging device has been powered on. Data that may be stored or written into memory 1188 may include data such as manufacturing date, date of last verification or quality control check, location of manufacture, i.e., may include name, city, state, street address and so forth, last control unit that the imaging device head was attached to, imaging device head diagnostic information, specific procedural settings for the imaging device head, or preferred settings for an operator or user, such as a surgeon. Data representing the above characteristics, or other indicia, of the imaging device may be recorded into memory within the imaging device.

The memory 1188 may be encryption protected so as to avoid tampering or unintended use and foreseeable misuse. It should be noted that a memory may be placed anywhere in the imaging device and not just the imaging device head without departing from the scope of the disclosure. The memory 1188 may comprise a permanent or semi-permanent portion allowing a varying degrees of data durability.

Figure 15:
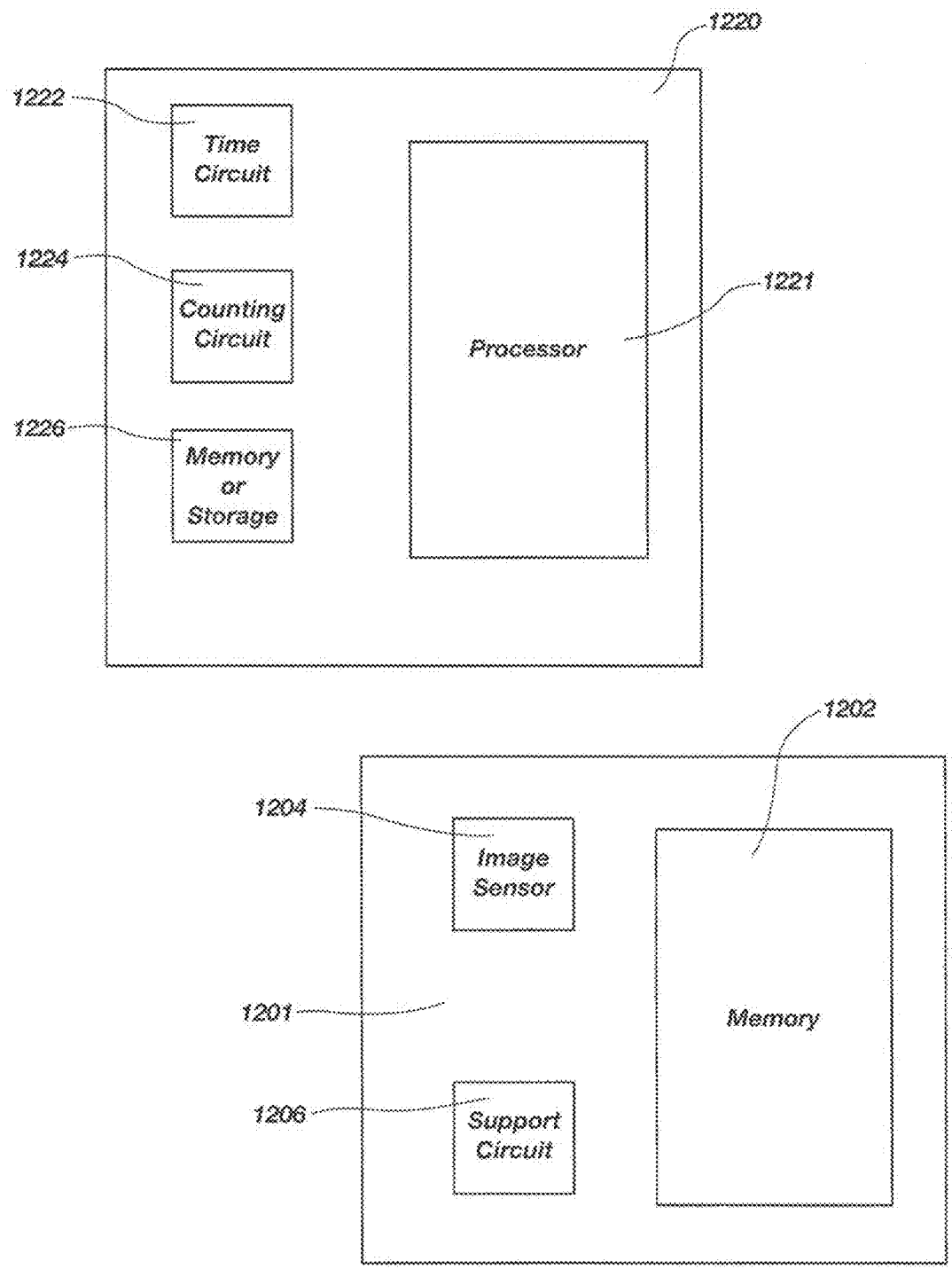
FIG. 15 is a layout view of an embodiment of an imaging system made in accordance with the teachings and principles of the disclosure.

Referring now to FIG. 15 an embodiment of a system for acquiring imagery in a sterilized environment will be discussed. The system may comprise an imaging device 1201 having a memory 1202, an image sensor 1204, and supporting circuitry 1206, including a processor. The imaging device 1201 may be an active device and may comprise a processor, a micro-processor or micro controller, a field programmable gate array (FPGA), active circuit, or a complex programmable logic device (CPLD). The system may further comprise and control unit 1220 having a processor 1221, time circuit or realtime clock 1222, a counting or incrementing circuit 1224 and a control unit memory 1226. The components will generally be provided in a housing, but are shown hear in block diagram form for simplicity and discussion purposes. It is contemplated that any of the above circuits can operate from either a control unit or an imaging device.

Figure 16:
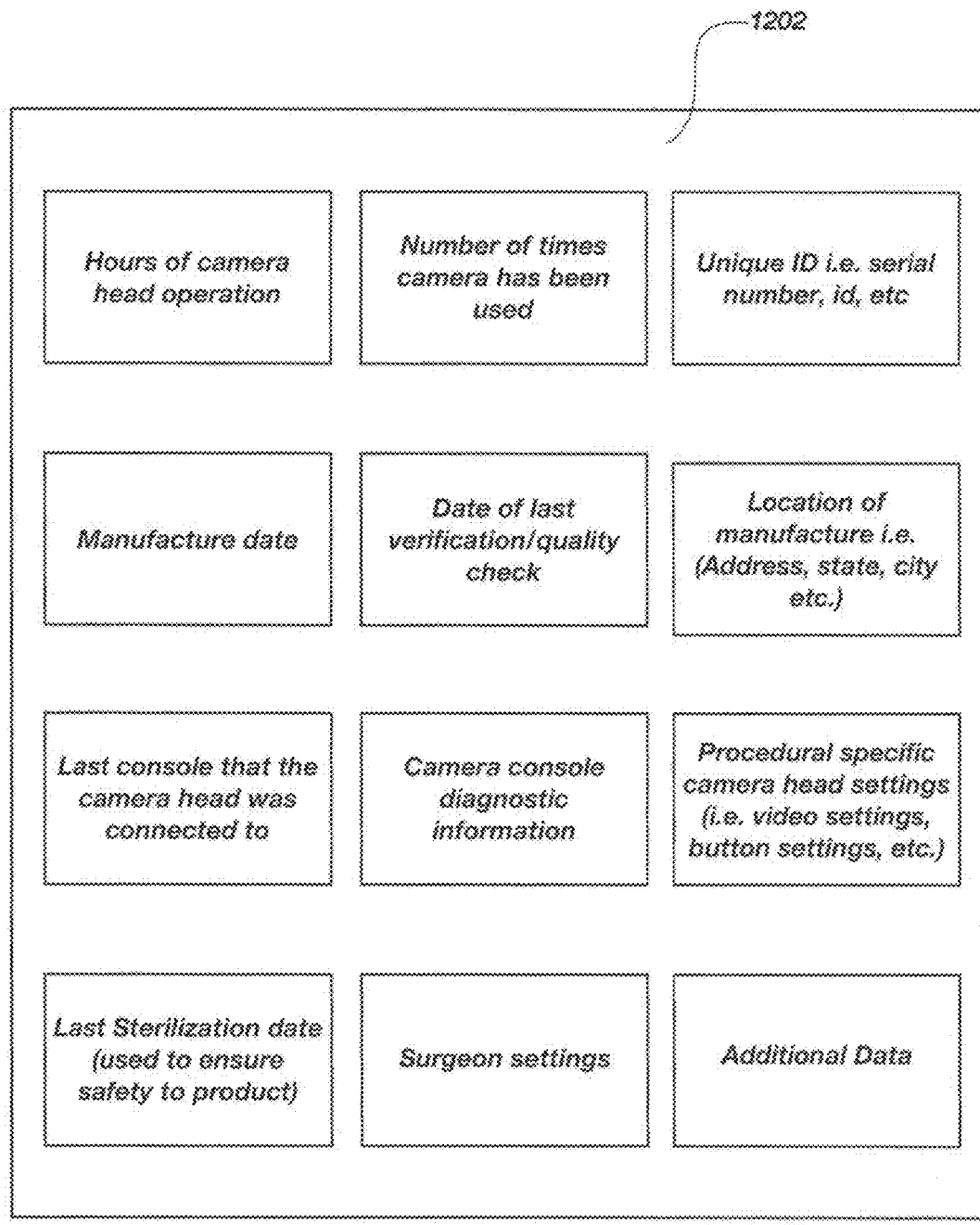
FIG. 16 is a schematic diagram of a memory of an embodiment of an imaging system made in accordance with the teachings and principles of the disclosure.

As can be seen in FIG. 16 the memory 1202 of the imaging device 1201 may comprise the following arrays of data storage:
a. Hours of camera head operation;
b. Number of times camera has been used;
c. Unique identification i.e. serial number, id, etc.;
d. Manufacture date;
e. Date of last verification/quality check;
f. Location of manufacture i.e. (Address, state, city etc.);
g. Last console that the camera head was connected to;
h. Camera console diagnostic information;
i. Procedural specific camera head settings (i.e. video settings, button settings, etc.);
j. Last Sterilization date (used to ensure safety to product); and
k. Surgeon or user settings.

Additional data may be stored within the memory 1202 that would enhance the imaging device and is considered to be within the scope of the disclosure.

Figure 17:
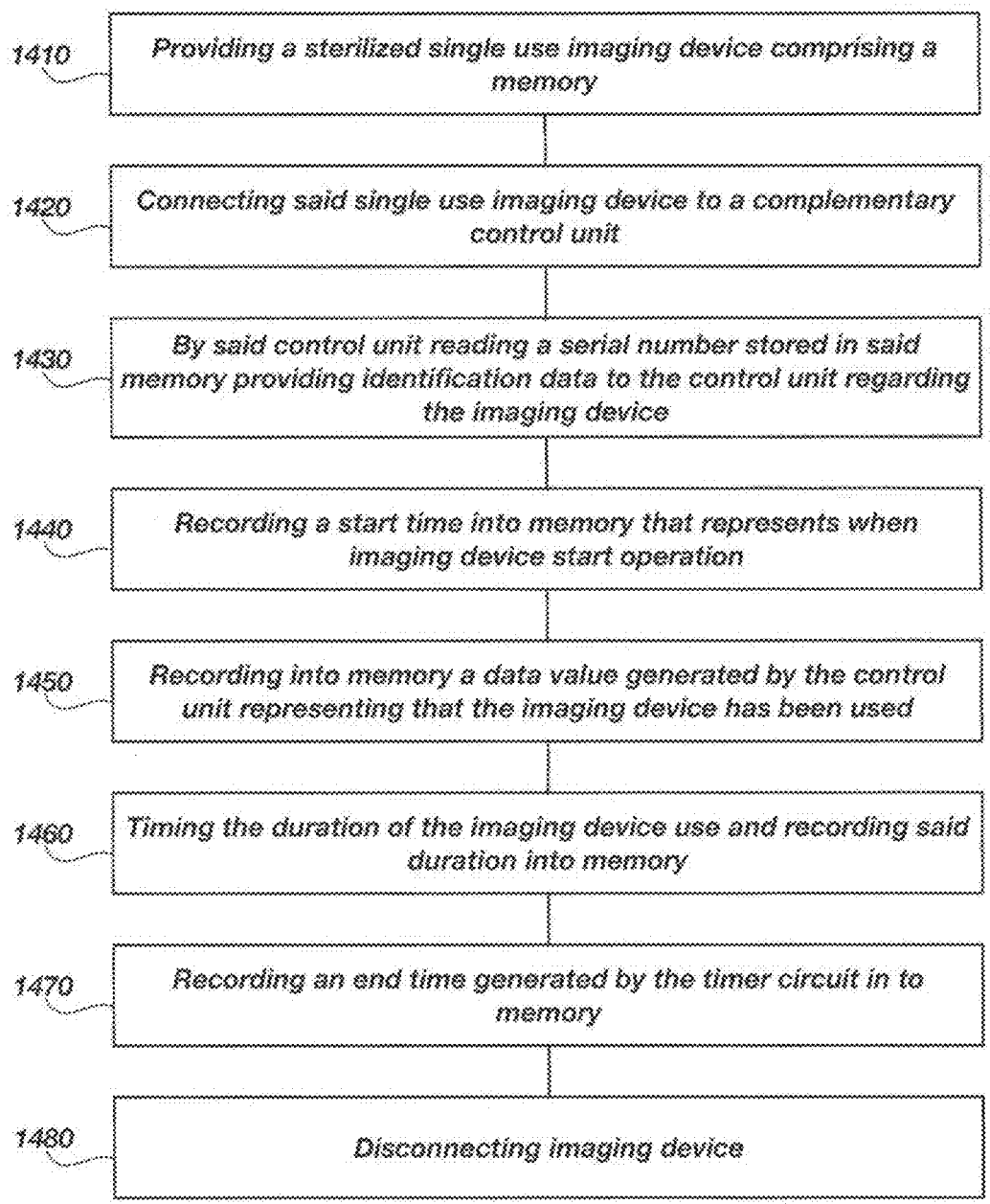
FIG. 17 illustrates an embodiment of a method in accordance with the teachings and principles of the disclosure.

With reference to FIG. 17, a method of using an imaging system consistent with the embodiments disclosed herein will be discussed. In use, a sterilized single use imaging device 1201 will be provided that may comprise memory 1202 at 1410. At 1420 a user may connect the single use imaging device 1201 to a complementary control unit 1220 both electronically and physically. At 1430 the control unit 1220 may initiate a process of reading memory 1202 and registers the serial number of the imaging device 1201. At 1440 the system causes a value to be recorded into memory 1202 indicating that the imaging device 1201 has been used. At 1450 the system records into memory 1202 the date and time the imaging device 1201 is connected to the control unit 1220. At 1460 a timing process is initiated by the control unit from the base line time recorded at 1450 and tracks or times the duration that the imaging device 1201 is used and the duration is recorded into memory 1202 at 1470. After use, the imaging device 1201 is disconnected from the control unit 1220 at 1480 and then discarded for renewal or reclamation.

Figure 18:
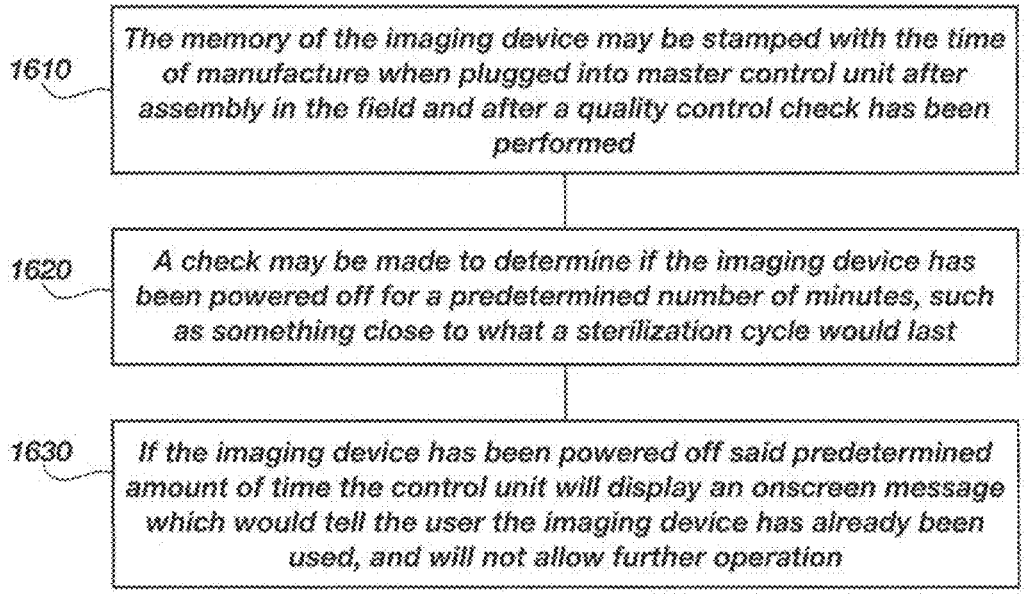
FIG. 18 illustrates an embodiment of a method in accordance with the teachings and principles of the disclosure.

With reference to FIG. 18 an alternative embodiment of a method of use will be discussed illustrating safety settings of the embodiment. At 1610 the memory imaging device head may be stamped with time of manufacture when it is plugged into the master control unit or master console after assembly in the field, i.e., in an operating room, and after a quality control check has been performed. At 1620 a check may be made to determine if the imaging device has been powered off for a predetermined number of minutes, such as a time frame that is close to what a typical sterilization cycle would last. At 1630, if the imaging device has been powered off the predetermined amount of time the control unit will display an onscreen message telling the user the imaging device has already been used, and will not allow further operation, such that no image will be produced through video feed. This feature will ensure the imaging device, i.e., the camera, will not be used more than one time per sterilization cycle. This feature also protects the patient and the doctor from an invalid or unsafe use and foreseeable misuse.

Figure 19:
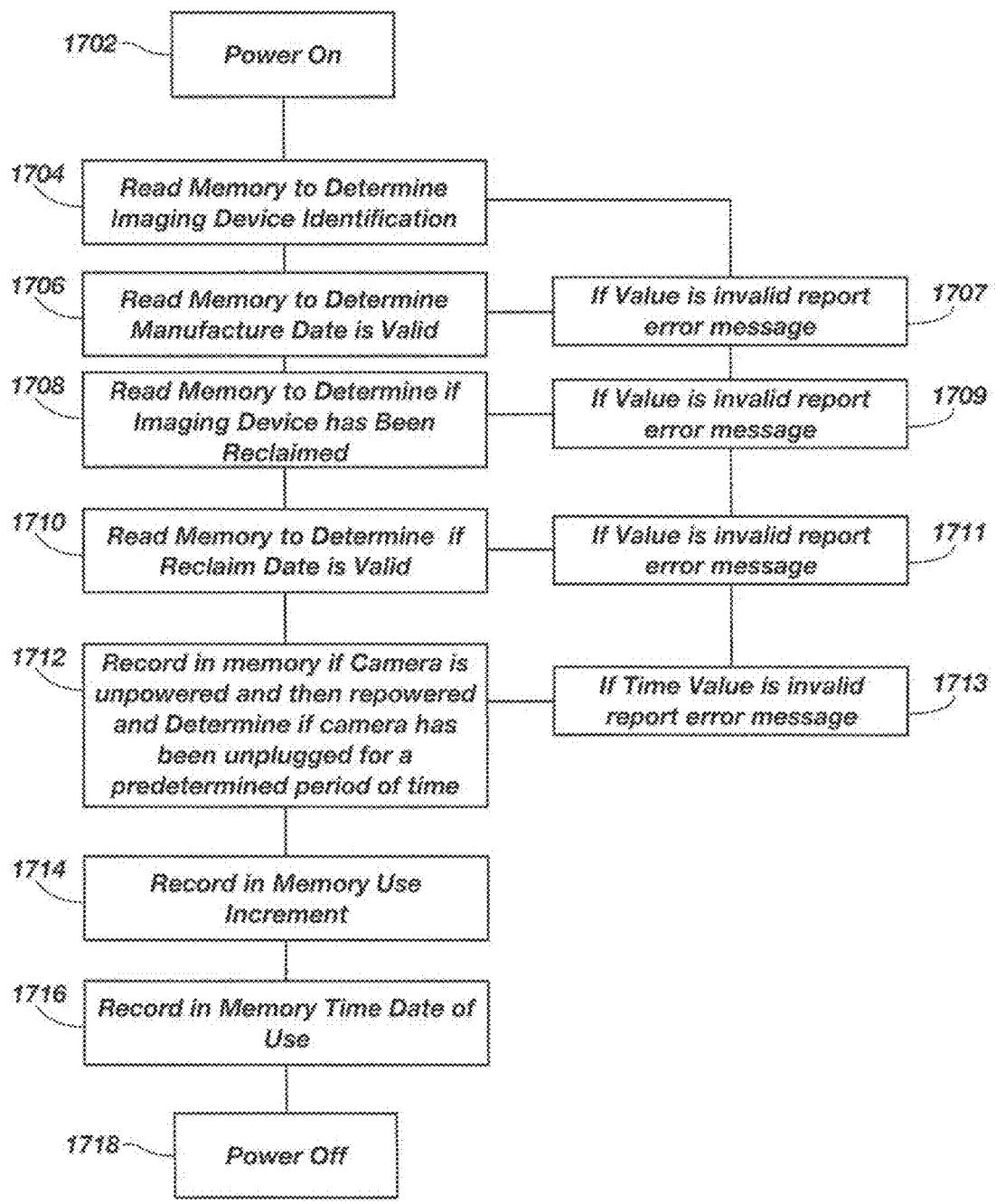
FIG. 19 illustrates an embodiment of a method of use according to the teachings and principles of the disclosure.

Referring to FIG. 19 an embodiment of a method of use will be discussed. During use, an imaging device may be connected to a control unit. Upon connection, an electronic communication connection is formed between the imaging device and the control unit. At 1702 the imaging device may be powered on by power supplied by the control unit. At 1704 a processor in the control unit may cause data regarding imaging device identification that may be stored in a memory within the imaging device to be read. At 1706 a processor in the control unit may cause data regarding the manufacturing date of the imaging device to be read from memory within the imaging device. The processor in the control unit may then compare the data to a predetermined data value range. At 1707 an error message may be displayed if the read data is outside the predetermined data value range and the imaging device will be stopped from operating. At 1708 a processor in the control unit may cause data regarding the reclamation of the imaging device to be read from memory within the imaging device. The data regarding reclamation of the imaging device may include data representing whether or not the imaging device has been previously used. The processor may then compare the data to a predetermined data value range. At 1709 an error massage may be displayed if the read data is outside the predetermined data value range and the imaging device will be stopped from operating. At 1710 a processor in the control unit may cause data regarding the reclamation date of the imaging device to be read from memory within the imaging device. The processor may then compare the data to a predetermined data value range. At 1711 an error massage may be displayed if the read data is outside the predetermined data value range and the imaging device will be stopped from operating. At 1712 a processor in the control unit may cause usage information of the current procedure to be monitored to note whether imaging device has been unpowered for a predetermined period of time and then re-powered. If this condition occurs it is possible that the imaging device has been tampered with or that an attempt has been made to sterilize the imaging device and use it a second time. The predetermined period of time may correspond to the amount of time a typical sterilization process would normally take. The processor then compares the data to a predetermined data value range. At 17013 an error massage may be displayed if the data read is outside the predetermined data value range and the imaging device will be stopped from operating. At 1714 a processor in the control unit may cause a value to be placed in memory in the imaging device indicating that the imaging device has been used. At 1716 a processor in the control unit may cause the date and time of use to be recorded in memory in the imaging device. Additional information may be recorded into the memory of the imaging device such as, for example, duration of use, procedure settings, and user settings and any other data suitable for recording to memory. The imaging device may be disconnected from the control unit and thereby powered off at 1718.

Referring now to FIGS. 20 through 23, embodiments of a view optimizing assembly 10 for use in association with a state of the art laparoscope 12 are illustrated. The laparoscope 12 may possess a zero degree (blunt) shaft tip or the laparoscope 12 may possess an angled shaft tip (e.g., between a range of about a thirty degree shaft tip or about a forty-five degree shaft tip). The components of the view optimizing assembly 10 may be made from plastic materials (extruded and/or molded), but other suitable materials, such as metal or a composite material, or combinations thereof could also be used.

As can be seen in the figures, an image sensor may be disposed at or near the tip or lumen 14 as previously discussed. An embodiment may also comprise a camera head attached near locking feature 28 wherein the camera head comprises video and other controls. An embodiment may comprise a camera control unit and or a light source. Light may be transmitted near to the tip of lumen 14 via fiber optics or other means. Fiber optics and control cables may be routed through openings in the wall of lumen 14. Fiber optics and control cables may be routed through openings 36, 34, 38, 40, or 42.

As will be described in greater detail, the view optimizing assembly 10 may operate to facilitate intra-operative defogging, surgical debris deflection, and cleaning of a laparoscope lens during minimally invasive surgery, while also maintaining visualization of the surgical site. The view optimizing assembly 10 is intended to be a single-use, disposable laparoscopic accessory. The view optimizing assembly 10 may be a sterile accessory for immediate set up and use on a sterile operating field.

Continuing to refer to FIGS. 20 through 23, the view optimizing assembly 10 may comprise a multi-lumen sheath assembly 14, which mounts over the shaft of the laparoscope 12. The end of the shaft may be sized, shaped and configured to match the size, shape and configuration of the corresponding laparoscope 12, having either a blunt tip or an angled tip. The assembly 10 may include a tubing set 16 to connect the sheath 14 to an existing anhydrous carbon dioxide (CO2) insufflation circuit.

In use, the view optimizing assembly 10 makes possible the practice of a surgical method for maintaining clear visualization of the surgical site without removing the laparoscope 12 from the abdominal cavity for the purpose of cleaning or de-fogging its lens. Furthermore, the view optimizing assembly 10 also makes possible a surgical method for maintaining clear visualization that includes the ability to make a quick exchange of laparoscopes having different operating characteristics (e.g., laparoscopes with different tip angles, lengths, or diameters) entirely on the sterile operating field and without interference with the preexisting surgical set-up on the sterile operating field. The view optimizing assembly 10 may integrate with the existing suite of minimally invasive instrumentation. The view optimizing assembly 10 does not interfere with the surgical set-up, and it requires minimal change in the process or practice of a surgical operating room (OR) team.

Figure 20:
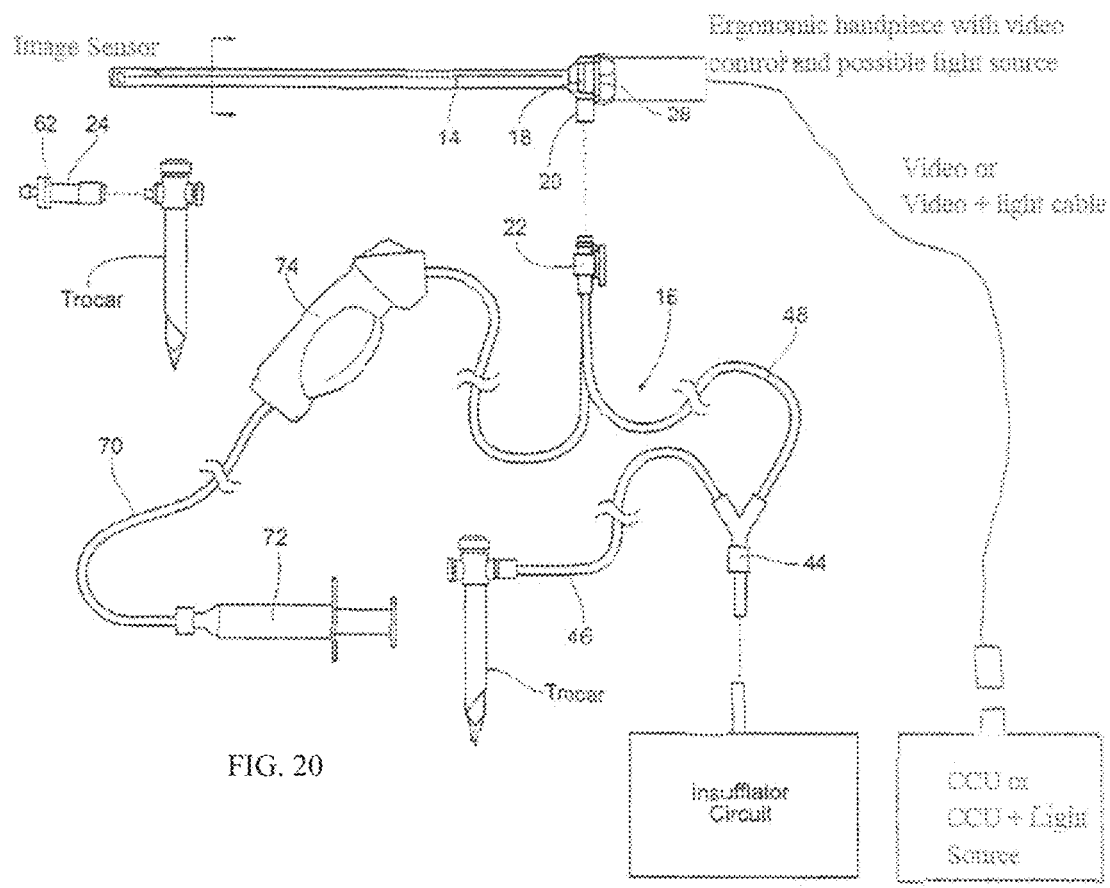
FIG. 20 is a schematic view of a view optimizing assembly for use with a laparoscope having a zero degree shaft tip and made in accordance with the teachings and principles of the disclosure.
Figure 21:
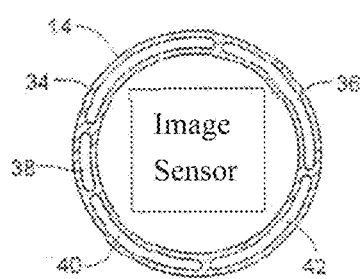
FIG. 21 is a section view of the sheath, showing internal fluid flow lumens, taken generally along line 20B-20B in FIG. 20.
Figure 22:
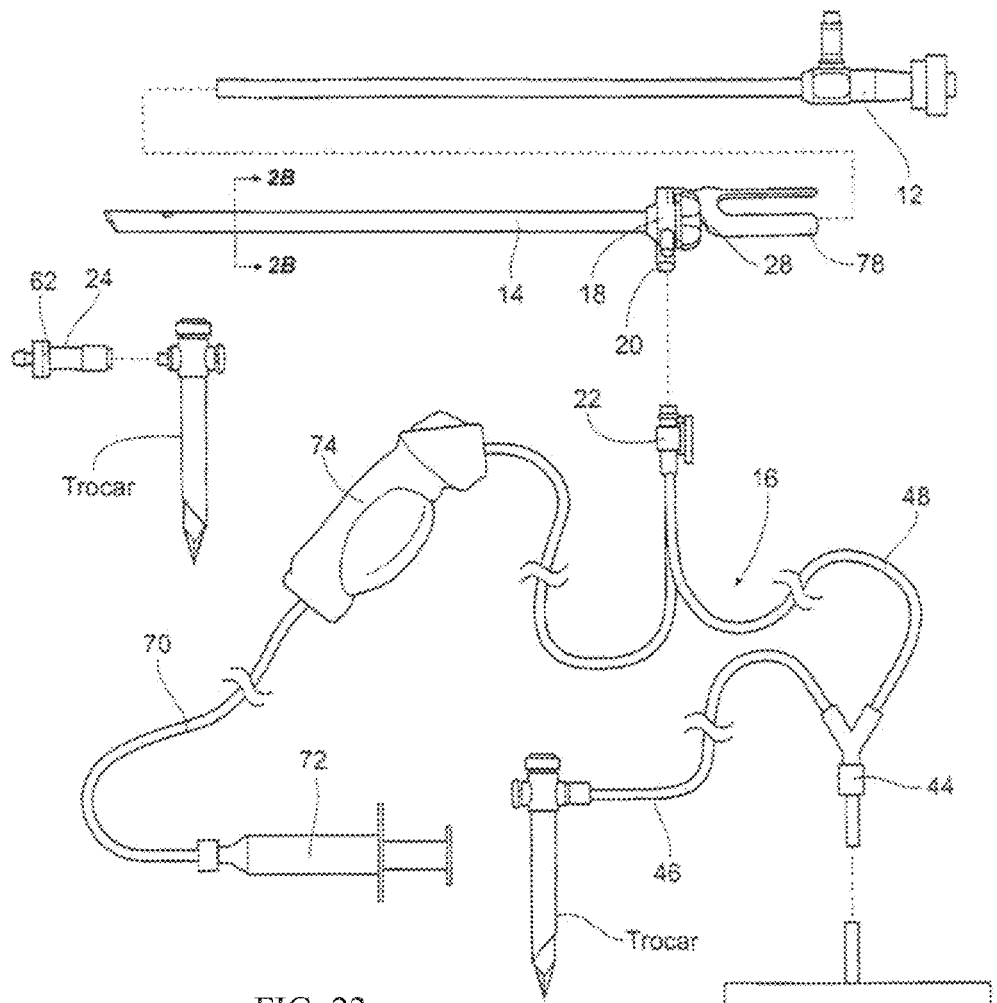
FIG. 22 is a schematic of a view optimizing assembly for use with a laparoscope having an angled shaft tip and made in accordance with the teachings and principles of the disclosure.
Figure 23:
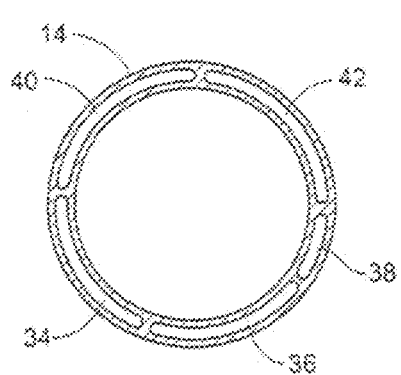
FIG. 23 is a section view of the sheath, showing internal fluid flow lumens, taken generally along line 22B-22B in FIG. 22.

The view optimization assembly 10 may be packaged in sterile peel away pouches. As shown in FIGS. 20 and 22, the pouches may contain the components of the view optimization assembly 10, including the sheath 14 and a manifold 18 that may be assembled to the sheath 14 and that may comprise a quick exchange coupling 20, the tubing set 16, which may comprise a quick exchange coupler 22 that mates with the quick exchange coupling 20 on the manifold 18, and (optionally) a vent device 24.

As shown in FIGS. 20 and 22, the sheath 14/manifold 18 assembly may include a sheath 14 that is sized, shaped and configured to receive a laparoscope 12 having a prescribed tip angle, length, and diameter. The sheath 14 may include a stop 26 (see FIGS. 25 and 27) formed adjacent the distal end of the sheath 14. The stop 26 prevents advancement of the laparoscope 12 beyond the distal end of the sheath 14, so that lens at the distal end of the laparoscope 12 rests in a desired, generally coterminous or abutting alignment with the distal end of the sheath 14. The sheath 14 may also include a locking collar 28 at its proximal end to frictionally engage the laparoscope 12 and resist axial withdrawal of the laparoscope 12 from the sheath 14.

In use, it is expected that the laparoscope 12 will be inserted into the sheath 14 by a scrub nurse during set-up for the operation. The assembled laparoscope 12 and sheath 14 will then be handed as a unit to personnel at the operating room ("OR") table at the desired time. The laparoscope 12 may then be connected by personnel at the OR table in conventional fashion to a light cable 30 (which directs light to illuminate the operative field) and the camera cable 32 (which takes the image from the scope and displays it on monitors in the OR). The sheath 14 may be sized, shaped and configured not to interfere with this normal set-up of the laparoscope 12.

In use, the assembled laparoscope 12 and sheath 14 are placed as a unit through a trocar into the body cavity (e.g., the abdominal cavity), for viewing the surgical procedure as it is performed.

As shown in FIGS. 20 and 22, the sheath 14/manifold 18 assembly may also include the manifold 18 at the proximal end of the sheath 14. The manifold 18 may operate to communicate with multiple lumens (34 to 42) (there are five lumens illustrated in the figures, but more or less lumens may be utilized without departing from the scope of the disclosure) formed within the wall of the sheath 14 (see FIGS. 21 and 23). In use, the lumens 34 to 42 function to convey anhydrous CO2 to the distal end of the sheath 14; vent or exhaust air from the distal end of the sheath 14 through the manifold 18; and, if desired, convey sterile fluid and bursts of air to the distal end of the sheath 14. In a representative embodiment (see FIGS. 21 and 23), two lumens 34 and 36 may be dedicated to the transport of CO2; two lumens 40 and 42 may be dedicated to venting; and one lumen 38 may be dedicated to the transports of sterile fluid or air.

As previously described, the tubing set 16 may comprise a quick exchange coupler 22 that mates with the quick exchange coupling 20 on the manifold 18. The tubing set 16 may include lengths of flexible medical grade tubing with individual end couplers (best shown in FIGS. 20 and 22) that connect to an existing CO2 insufflation circuit and, if desired, a source of sterile fluid (saline or sterile water, preferably with a "surface active agent") on the sterile operating field (e.g., a bag or a syringe). The tubing set 16 may include a Y-connector 44 that divides the anhydrous CO2 output of the insufflation circuit in a first branch 46 for coupling to an insufflation trocar inserted in the body cavity (as will be described later), and a second branch 48 coupled to the quick exchange coupler 22. The second branch 48 diverts a small portion of the CO2 output (e.g., 20% or less) to the quick exchange coupler 22.

The quick exchange coupler 22 may include a one way check valve 50 that communicates with the second branch 48 of the tubing set 16. In an embodiment, the check valve 50 may comprise a ball valve. Insufflation pressure normally presses the ball valve 50 against a ball valve seat 52. A projection 54 in the manifold 18 displaces the ball valve 50 from the valve seat 52 when the quick exchange coupler 22 mates with the quick exchange coupling 20 on the manifold 18. Unseating the ball valve 50 opens flow communication through the check valve 50. In the absence of coupling the quick exchange coupler 22 on the tubing set 16 to the quick exchange coupling 20 on the manifold 18, the check valve 50 remains closed, normally blocking flow of CO2 through the second branch 48. Thus, the tubing set 16 accommodates the set-up of the supply of the entire CO2 output to a insufflation trocar through the tubing set 16, separate and independent of the connection of the tubing set 16 to the manifold 18 of the sheath 14.

A latch 56 carried on a spring-biased button 58 on the quick exchange coupler 22 "clicks" into a detent 60 on the quick exchange coupling 20 on the manifold 18 to reliably lock the coupler 22 and coupling 20 together for use, opening the check valve to flow CO2 through the second branch 48. Depressing the button 58 allows the quick exchange coupler 22 and coupling 20 to be separated, and the check valve 50 will close in response to insufflation pressure in the second branch 48.

Connection of the quick exchange coupling 20 on the manifold 18 to the quick exchange coupler 22 on the tubing set 16 is intended to occur at the OR table in the normal course, after the laparoscope 12 is connected to the light cable 30 and the camera cable 32. Upon coupling, the one way check valve 50 is opened, and the manifold 18 directs the small portion of CO2 from the CO2 insufflation circuit. Disconnection of the quick exchange coupling 20 on the manifold 18 to the quick exchange coupler 22 on the tubing set 16 is also intended to occur at the OR table in the normal course, after a removal and/or exchange of a laparoscope 12.

The vent device 24 (see FIGS. 20 and 22) may comprise a tube with an inline membrane 62 that restricts air flow through the tube. A proximal end of the tube is sized and configured to couple to a stopcock valve of a conventional trocar, as will be described later. In use, the vent device 24 provides a controlled leak of CO2 from the operating cavity, as will also be described in greater detail later.

Figure 24:
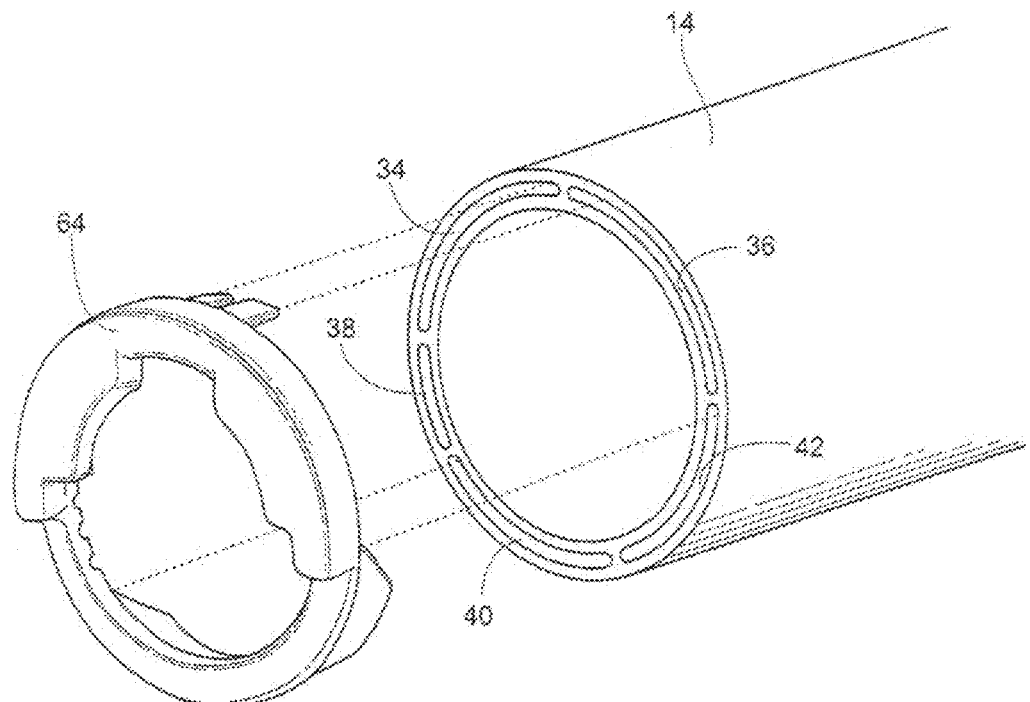
FIGS. 24 and 25 are enlarged, exploded views of the deflector assembly for use with a laparoscope having a 0 degree shaft tip and made in accordance with the teachings and principles of the disclosure.
Figure 25:
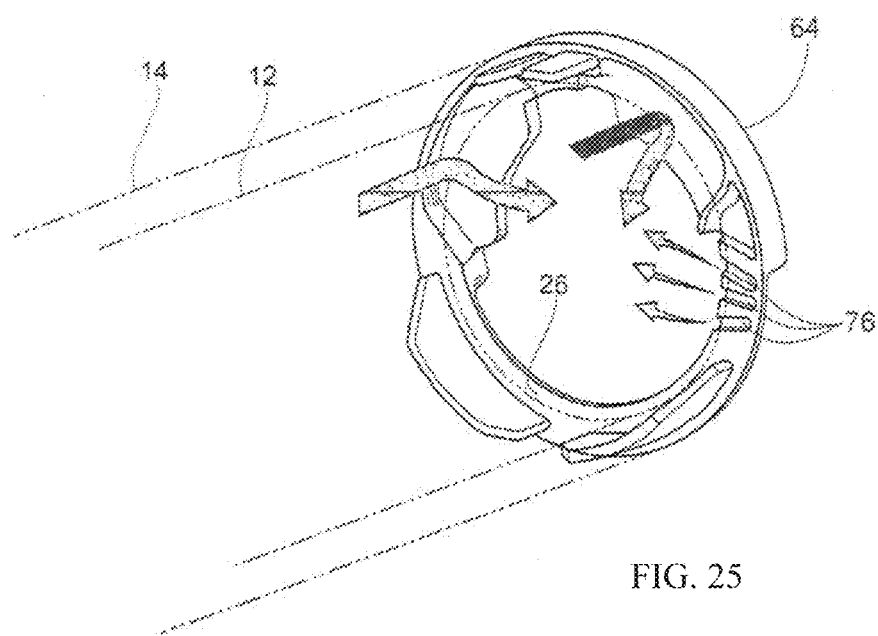
Figure 26:
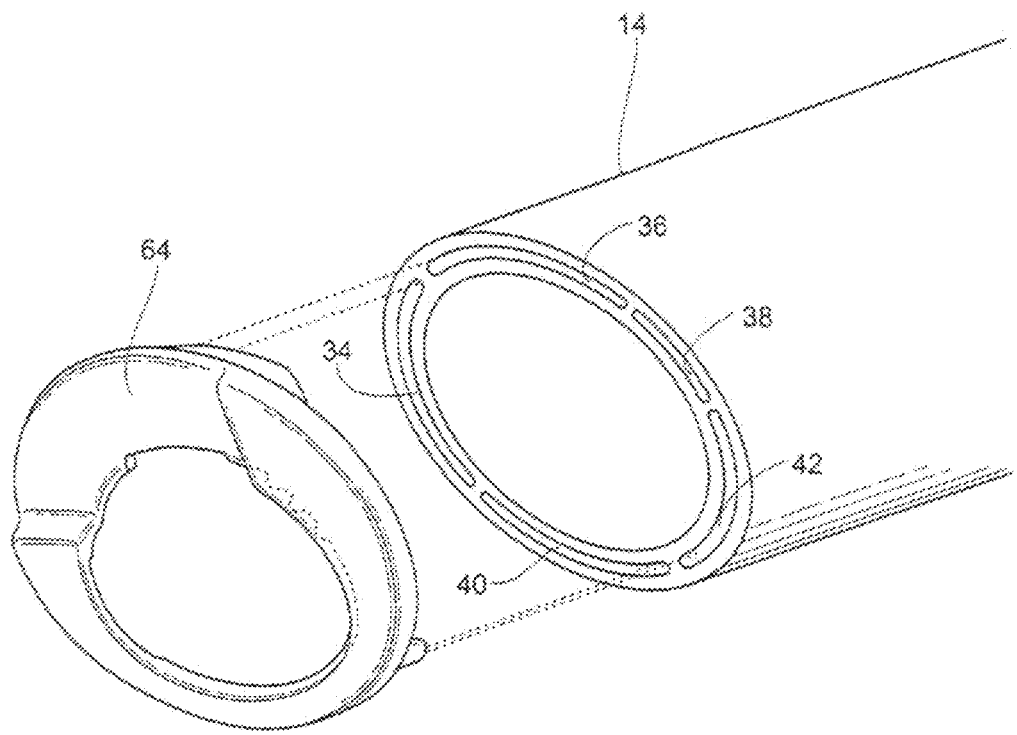
FIGS. 26 and 27 are enlarged, exploded views of the deflector assembly for use with a laparoscope having an angled shaft tip and made in accordance with the teachings and principles of the disclosure.
Figure 27:
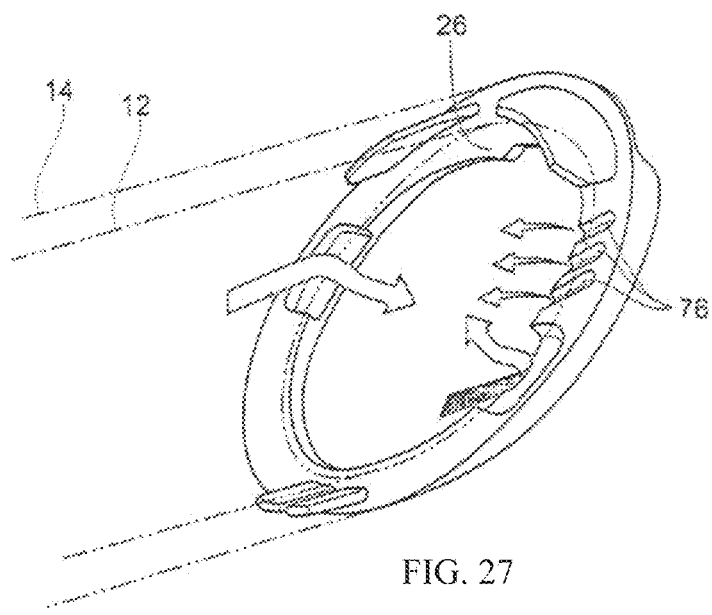

The sheath 14 may include at its distal end a deflector assembly 64 (see FIGS. 24 and 25 for a blunt shaft tip and FIGS. 26 and 27 for an angled shaft tip). The deflector assembly 64 may project a predetermined distance beyond the distal end of the sheath 14, and thus also a predetermined distance beyond the lens at the distal end of the laparoscope 12. The deflector assembly 64 communicates with the lumens in the sheath 14. The deflector assembly 64 may be sized, shaped and configured to direct the small portion of the CO2 from the insufflation circuit in a prescribed flow path and flow velocity continuously across the laparoscopic lens.

The desired flow path and flow velocity of CO2 established by the deflector assembly 64 continuously across the laparoscopic lens creates a "wind shear." The wind shear path of anhydrous CO2 prevents fogging. The desired flow path and flow velocity of CO2 established by the deflector assembly 64 continuously across the laparoscopic lens may also advantageously serve to deflect smoke and surgical debris away from the laparoscopic lens during surgery.

The size, shape and configuration of the deflector assembly 64 may be defined and constrained by several, sometimes overlapping considerations, including, but not limited to: (I) prescribed physical characteristics, which are imposed due to the need to access the operating environment in as minimally invasive manner as possible and to be compatible with state of the art laparoscopes and other laparoscopic surgical instruments and techniques; (ii) prescribed pneumatic characteristics, which are imposed due to the need to create a particular "wind shear" effect in terms of the flow path and flow velocity of CO2 across the laparoscopic lens; and (iii) prescribed optical characteristics, which are imposed due to the need to prevent interference with the field of view and the visualization of the operating field by the laparoscope 12.

The size, shape and configuration requirements for minimally invasive access compatible with state of the art laparoscopic instrumentation and techniques should be carefully considered. These requirements impose constrains upon the minimum inside diameter of the sheath 14 as well as the maximum outside diameter of the sheath 14. Because state of the art laparoscopes are provided with different shaft diameters, lengths, and lens configurations, the sheath dimensions and configuration change for compatibility with such laparoscopes. The view optimizing assembly 10 may include a family of sheath 14/manifold 18 assemblies that are sized, shaped and configured differently to accommodate different classes of laparoscopes to ensure there is a potential for compatibility with the families of state of the art laparoscopes that are in use.

For example, state of the art laparoscopes include 10 mm laparoscopes, 5 mm laparoscopes. Within these classes or sizes, there are zero degree shaft tips, thirty degree shaft tips, and forty-five degree shaft tips. Further, within these classes of laparoscopes, manufacturing tolerances typically vary from scope to scope, as well as from manufacturer to manufacturer. A given sheath 14/manifold 18 assembly for a given laparoscope class (e.g., 10 mm or 5 mm) takes these typical manufacturing and manufacturer variances into account, and is sized and configured to fit the largest scope variance encountered within a given laparoscope class.

To maximize the fluid flow lumen area within the sheath 14, the minimum inside diameter of a given sheath 14 should closely conform to the maximum outside diameter of the shaft of the particular state of the class of laparoscope 12 selected for use, which the sheath 14 must accommodate in a smooth, sliding fit. Further, a gap between the outside diameter of the laparoscope shaft and the inside diameter of the sheath 14 should be minimized to avoid the transport and leakage of blood and fluids from the operating field. Still further, minimizing the gap also assures that the laparoscope 12 self-centers in the sheath 14, thereby assuring faithful and accurate visualization through the laparoscope lens.

For example, for a typical laparoscope 12 in the 10 mm class, which measures 0.392 inch, the inside diameter of the sheath 14 is manufactured to 0.405 inch, providing a gap thickness of 0.0064 inch. For a 5 mm laparoscope 12 in the 5 mm class, which measures 0.196 inch, the inside diameter of the sheath 14 is manufactured to 0.218 inch, providing gap thickness of 0.011 inch.

The maximum outside diameter of the sheath 14 for minimally invasive access should take into account the minimum inside diameter of the trocar, which the maximum outside diameter cannot exceed. For example, for a typical 10 mm trocar that measures 0.509 inch, the outside diameter of the sheath 14 is manufactured to 0.486 inch, providing a gap thickness of 0.0115 inch. For a typical 5 mm trocar that measures 0.324 inch, the outside diameter of the sheath 14 is manufactured to 0.300 inch, providing a gap thickness of 0.012 inch.

Given the particular size, shape and configuration constraints of the laparoscopic instrumentation and techniques used, it may be advantageous to maximize the outside diameter to the extent possible. The reason is the inside and outside diameters of the sheath 14 together define the wall thickness for the sheath $S_W$. The wall thickness $S_W$, together with the length of the sheath 14, in turn, define the maximum area available for the transport of the CO2 and fluids by the sheath 14. The area of the fluid flow lumen or lumens dedicated to the supply of CO2, in turn, defines the maximum flow rate of the CO2 directed by the deflector assembly 64. The flow rate should be sufficient at a minimum, given the output of the insufflator selected for use, to supply anhydrous CO2 across the lens of the laparoscope 12 sufficient to prevent fogging. Also affecting the effectiveness of the CO2 to defog the lens, is the water content of the anhydrous CO2. Given the same flow rate, the less water that is present in the anhydrous CO2, the greater is the defogging capacity of the assembly. Further, the flow rate desirable should also be sufficient to deflect smoke and surgical debris away from the viewing field of the laparoscopic lens during surgery, so that the anhydrous CO2 directed by the deflector assembly 64 both defogs and deflects debris.

Medical grade CO2 for use with conventional insufflators is typically 99% pure, that is, no more than 1% of the gas is other than CO2, and such medical grade anhydrous CO2 generally has a maximum moisture content of 25 parts per million by volume. Typically, a state of the art insufflator circuit delivers anhydrous CO2 at a max flow rate of about 20 liters per hour. Typically, the insufflator circuit will sense pressure in the circuit and cycle off when the sensed pressure is at or above 15 mmHg and cycle on when the sensed pressure is below 15 mmHg.

Given the above sheath dimensions, and given the supply of typical medical grade anhydrous CO2, a flow rate of at least about 1.0 liters per minute is used to achieve this result. Given the above dimensions, and the supply of typical medical grade anhydrous CO2, a flow rate less than 0.8 liters per minute is not sufficient to prevent significant accumulation of moisture on the laparoscope lens.

In an embodiment, for a sheath 14 having an inside diameter of about 0.405 inch and an outside diameter of about 0.486 inch, and a length of about 11.25 inch (which accommodates passage of a typical 10 mm laparoscope and its own passage through a conventional trocar) (i.e., $S_W$=0.081 inch), the total area available in the sheath wall is about 0.056 square inches. Based upon required structural support within the wall (inside, outside, and radial) the total available area for lumens to transport fluids is about 0.027 square inch.

In an embodiment, the total lumen area is occupied by a plurality of lumens, for example five lumens 34, 36, 38, 40, 42—two for transporting CO2 (34 and 36), one for sterile fluid (38), and two for passive exhaust air venting (40 and 42).

The area of each lumen can be maximized by selection of lumen geometry. In an embodiment, lumen geometry is generally triangular or pie shaped with rounded corners. The radial walls that separate the lumens within the sheath 14 are sized to minimize the spacing between the lumens. However, it will be appreciated that the lumen geometry may be modified without departing from the scope of the disclosure.

In an embodiment, CO2 transport is accomplished by two lumens 34 and 36 that extend about 175 degrees about the outer circumference of the sheath 14 and comprising a flow area of about 0.013 square inches. Sterile fluid transport is accomplished by one lumen 38 comprising a flow area of about 0.003 square inches. Exhaust air venting is accomplished by two lumens 40 and 42 comprising a flow area of about 0.011 square inches. The distal openings of the exhaust lumens 40 and 42 are spaced from the distal end of the sheath, to prevent uptake of blood and fluids.

The deflector assembly 64 may overhang the laparoscopic lens by a prescribed transverse distance, defining a deflection width X, sufficient to change the direction of CO2 flowing axially through lumens of the sheath 14 (i.e., along the axis of the laparoscope shaft) into a non-axially, transverse path across the laparoscopic lens (i.e., at an angle relative to the axis of the laparoscope shaft). Still, the distance of the deflection width X should not extend to the point that is obstructs the field of the view of the laparoscopic lens. This is an example where a pneumatic characteristic of the deflector assembly 64 overlaps with an optical characteristic. Further optical characteristics will be described in greater detail below.

The deflector assembly 64 may also project axially beyond the distal terminus of the sheath 14 by a prescribed axial distance, defining an air channel distance Y, sufficient to maintain the CO2 flowing along the path bounded by the deflection width X at a distance sufficiently close (proximal) to the laparoscopic lens to achieve the desired shear flow effect, but without forming an abrupt flow bend that can lead to a reduction in the desired CO2 flow velocity.

Together, the deflection width X and the channel distance Y define the pneumatic characteristics of the deflection assembly. At the desired minimum flow rate, the pneumatic characteristics create a flow path that conveys CO2 continuously across the laparoscopic lens at the desired flow velocity, in shorthand called the "wind shear." The pneumatic characteristics of the CO2 "wind shear" across the laparoscopic lens prevent fogging, as well as deflect smoke and surgical debris away from the viewing field of the laparoscopic lens during surgery.

Together, the pneumatic characteristics defined by the deflection width X and the channel distance Y create an exit angle $A_{EXIT}$, measured between the plane of the laparoscopic lens and the terminal edge of the deflector assembly 64. The exit angle $A_{EXIT}$ should be less than a maximum angle of 45 degrees, else the flow path of the CO2 will not pass sufficiently both across and proximal to the laparoscopic lens. To maintain a desired exit angle $A_{EXIT}$, the channel distance Y should be at least equal to the wall thickness of the sheath $S_W$ and should not exceed 1.5 times the wall thickness of the sheath $S_W$. The deflection width X should be at least equally to two times the channel distance Y, but not extend into the field of view of the laparoscopic lens.

The optical characteristics of the deflector assembly 64 are selected, at least in part, (I) to not block or reduce the illuminated image of the operating field provided by the laparoscope 12; (ii) not decrease the intensity of the illumination provided by the laparoscope 12 on the operating field; and (iii) prevent reflection of illumination light at the lens of the laparoscope 12.

As discussed above, the maximum deflection width X takes into account one of the desirable optical characteristics; namely, the deflection width X should not obstruct the field of the view of the laparoscopic lens.

To prevent the decrease of the illumination, the deflector assembly 64 may be made from a material having high light transmission properties (i.e., transparency), to not interfere with the passage of light through the light cable 30 onto the operating field as well as the passage of the reflected image conveyed to the camera cable 32 of the laparoscope 12.

Furthermore, the material and surface finish of the deflector assembly 64 must pose minimal reflectively to light. In a representative embodiment, the deflector assembly 64 may be made from Bayer Makrolen Rx1805 with a surface finish defined as SPI/SPE A-3.

As before described, CO2 transport may be accomplished by two lumens 34 and 36 that extend about 175 degrees about the outer circumference of the sheath 14. For a zero degree shaft tip (see FIGS. 5 and 24), the orientation of the deflector assembly 64 relative to the laparoscopic lens is not critical. However, for angled shafts (e.g., thirty degree shaft tips and forty-five degree shaft tips) (see FIG. 26), the orientation of the deflector assembly 64 relative to the laparoscopic lens should be considered.

As FIG. 26 shows, the angled tip of a typical laparoscope 12 has a high end 66 and a low end 68. The lens slopes at the prescribed angle between the high end 66 and the low end 68. In a laparoscope 12 having a angled tip, the illumination cable 30 (transmitting light onto the operating field) is located at the high end 66 of the angled tip, and the camera cable 32 (transmitting reflected light back to the camera) is located at the low end 68 of the angled tip. To provide the desired wind shear effect on an angled tip, it is critical that the deflector assembly 64 be oriented relative to the sloped laparoscopic lens such that the flow $CO_2$ is directed across the sloped plane of the lens from the low end 68 of the tip toward the high end 66 of the tip. In this arrangement, the defogging and debris deflection flow path originates proximal to the camera cable 32, which effectively comprises the eyes of the OR team. In this arrangement, the desired exit angle $A_{EXIT}$ directs the flow path of the $CO_2$ both sufficiently across and proximal to the sloped plane of the laparoscopic lens to achieve optimal defogging and debris deflection.

As previously explained, if desired, the tubing set 16 can also include, connected to the quick exchange coupler 22, a length of tubing 70 sized and configured for connection to a source 72 of sterile fluid, such as saline or sterile water (as shown in FIGS. 20 and 22). The sterile fluid may include in solution a "surface-active agent" that stabilizes mixtures of oil and water (e.g., fat) by reducing the surface tension at the interface between the oil and water molecules.

The quick exchange coupling 20 on the manifold 18 can also include a port to integrally connect the sterile fluid tubing 70 to direct the sterile fluid through the separate lumen 38 in the sheath 14 to the distal end of the sheath 14. The deflector assembly 64 directs the sterile fluid across the laparoscopic lens.

As shown in FIGS. 20 and 22, the sterile fluid tubing 70, if present, includes an in-line pumping device 72. The in-line pumping device 72 is sized and configured to be operated on demand by a person at the OR table to convey bursts of sterile fluid through the manifold 18 through the lumen to the distal end of the sheath 14. The in-line pumping device 72 and source can be integrated and comprise, e.g., a 20 cc syringe filled with sterile fluid and connected by a tubing luer-lock on the saline tubing. Alternatively, the in-line pumping device 72 and source can be separate and comprise, e.g., a bag of sterile fluid, a spike connection on the saline tubing of the tubing set 16 to open communication with the bag in conventional fashion, and an inline squeeze bulb or the like to pump burst of sterile fluid from the bag to the quick exchange coupler 22.

In this arrangement, the deflector assembly 64 is also sized and configured to direct the burst of sterile fluid in a desired path across the laparoscopic lens. The bursts of sterile fluid serve to flush debris off the end of the lens that may eventually accumulate, thereby cleaning the lens. Thereafter, bursts of air supplied through the deflector assembly 64 by a squeeze pump 74 in the tubing set 16 (see FIGS. 20 and 22) serve to clear residual fluid droplets off the lens and away from the deflector assembly 64 to maintain the desired flow path and flow velocity of $CO_2$ established by the deflector assembly 64 continuously across the laparoscopic lens, to maintain an acceptable view.

In an illustrative embodiment (see FIGS. 24 through 27), the deflector assembly 64 directs the bursts of sterile fluid or air along a plurality of individual diverging channels 76 (three are shown). The diverging channels 76 distribute the bursts of sterile fluid or air in a fanning pattern across the lens of the laparoscope 12. In the illustrative embodiment, the diverging channels 76 discharge the bursts of sterile fluid or air in a path that is generally ninety-degrees to the path of $CO_2$. This orientation of the sterile fluid path relative to the $CO_2$ path across the lens, optimal for effective lens cleaning, applies to both zero degree shaft tips and angled tips (e.g., thirty degree shaft tips and forty-five degree shaft tips).

The view optimizing assembly is well suited for use as a single-use disposable laparoscopic accessory device to facilitate intra-operative defogging and debris deflection (due to the flow of anhydrous $CO_2$) and cleaning of the lens of a laparoscope 12 (due to burst of sterile fluid, preferably including a "surface-active agent") during minimally invasive surgery, while also maintaining visualization of the surgical site.

In the foregoing Detailed Description, various features of the disclosure are grouped together in a single embodiment for the purpose of streamlining the disclosure. This method of disclosure is not to be interpreted as reflecting an intention that the claimed disclosure requires more features than are expressly recited in each claim. Rather, as the disclosure reflects, inventive aspects lie in less than all features of a single foregoing disclosed embodiment.

It is to be understood that the above-described arrangements are only illustrative of the application of the principles of the disclosure. Numerous modifications and alternative arrangements may be devised by those skilled in the art without departing from the spirit and scope of the disclosure and the disclosure is intended to cover such modifications and arrangements. Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. An imaging system for surgical use comprising:
   a control unit implemented as a device which is separate from an active imaging device which connects to the active imaging device to receive image data from the active imaging device;
   a hand held unit which includes within the hand held unit, the active imaging device, the active imaging device including a processor which
      checks to determine whether the active imaging device has been powered off for a predetermined period of time and,
      disables the functionality of the active imaging device based on determining that the amount of time during which the active imaging device has been powered off is equal to or exceeds a predetermined period of time,
   the active imaging device further including an electronic communication circuit which provides electronic communication between the active imaging device and the control unit which includes information indicating that the active imaging device has been disabled by the active imaging device;
   a lumen that is configured for laparoscopic use;
   an optical element corresponding to said lumen disposed about a distal tip of said lumen;
   a view optimizing assembly configured for delivering a fluid to a surface of said optical element, wherein said view optimizing assembly comprises:

a sheath sized and configured to receive said lumen;
a fluid flow channel within said sheath for directing a fluid toward said optical element;
an opening in said sheath sized for receiving said lumen therethrough;
a view opening in said sheath for providing said imaging sensor access to light;
wherein said system further comprises: a CMOS imaging sensor disposed within said lumen, wherein said CMOS imaging sensor is located substantially near the distal tip of said lumen.

2. The imaging system of claim 1, wherein the active imaging device includes a memory circuit containing data comprising a serial number which is stored in the memory circuit.

3. The imaging system of claim 1, wherein the active imaging device further comprises a counting circuit that causes a number of times the active imaging device has been used to be updated for each time the active imaging device is used.

4. The imaging system of claim 1, wherein the active imaging device further comprises a main circuit, wherein a timing circuit causes a date and time value to be recorded in an active imaging device memory when the main circuit is powered on and the timing circuit further records the amount of time the active imaging device is in use in the active imaging device memory.

5. The imaging system of claim 1, further comprising a memory which comprises:
data representing the number of hours of operation of the active imaging device;
data representing a unique identification code;
data representing a date of manufacture;
data representing a date of last verification/quality check;
data representing a location of manufacture;
data representing the last control unit to which the active imaging device was connected;
data representing diagnostic information;
data representing procedural specific settings; or
data representing specific settings for a specific user.

6. The imaging system of claim 1, wherein the optical element is implemented as a lens.

7. The imaging system of claim 6, wherein the optical element comprises a plurality of lenses.

8. The imaging system of claim 1, further comprising a light element disposed within the lumen.

9. The imaging system of claim 1, further comprising a locking mechanism that detachably locks the view optimizing assembly to the active imaging device.

10. The imaging system of claim 1, wherein the sheath comprises a plurality of fluid flow channels.

11. The imaging system of claim 9, wherein the view optimizing assembly further comprises a deflection assembly.

12. An imaging system for surgical use comprising:
a control unit implemented as a device which is separate from an active imaging device which connects to the active imaging device to receive image data from the active imaging device;
a hand held unit which includes within the hand held unit, the active imaging device, the active imaging device including a processor which
checks to determine whether the active imaging device has been powered off for a predetermined period of time and,
disables the functionality of the active imaging device based on determining that the amount of time during which the active imaging device has been powered off is equal to or exceeds a predetermined period of time,
the active imaging device further including an electronic communication circuit which provides electronic communication between the active imaging device and the control unit which includes information indicating that the active imaging device has been disabled by the active imaging device; and
a CMOS imaging sensor disposed within a housing of the hand held unit;
a lumen that is configured for laparoscopic use;
an optical element corresponding to said lumen disposed about a distal tip of said lumen;
a view optimizing assembly configured for delivering a fluid to a surface of said optical element, wherein said view optimizing assembly comprises:
a sheath sized and configured to receive said lumen;
a fluid flow channel within said sheath;
a deflector assembly for directing a fluid toward said optical element;
an opening in said sheath sized for receiving said lumen therethrough;
a view opening in said sheath for providing said imaging sensor access to light.

13. The imaging system of claim 12, wherein the active imaging device includes a memory circuit containing data comprising a serial number which is stored in the memory circuit.

14. The imaging system of claim 12, further comprises a memory containing data representing a number of times the active imaging device has been used, wherein the active imaging device further comprises a counting circuit that causes the number of times the active imaging device has been used to be updated each time the active imaging device is used.

15. The imaging system of claim 12, wherein the active imaging device further comprises a main circuit, wherein a timing circuit causes a date and time value to be recorded in memory when the main circuit is powered on and timing circuit further records the amount of time the active imaging device is in use in an active imaging device memory.

16. The imaging system of claim 15, wherein the memory comprises:
data representing the number of hours of operation of the active imaging device;
data representing a unique identification code;
data representing a date of manufacture;
data representing a date of last verification/quality check;
data representing a location of manufacture;
data representing the last control unit to which the active imaging device was connected;
data representing diagnostic information;
data representing procedural specific settings; or
data representing specific settings for a specific user.

17. The imaging system of claim 12, wherein the optical element is implemented as a lens.

18. The imaging system of claim 17, wherein the optical element comprises a plurality of lenses.

19. The imaging system of claim 12, further comprising a light element disposed within the lumen.

20. The imaging system of claim 12, further comprising a locking mechanism that detachably locks the view optimizing assembly to the active imaging device.

* * * * *